US009465009B2

(12) United States Patent
Tsuruno et al.

(10) Patent No.: US 9,465,009 B2
(45) Date of Patent: Oct. 11, 2016

(54) ULTRASONIC MEASURING DEVICE, ULTRASONIC IMAGE DEVICE, AND METHOD FOR PROCESSING ULTRASONIC IMAGE

(71) Applicant: SEIKO EPSON CORPORATION, Tokyo (JP)

(72) Inventors: Jiro Tsuruno, Nagano (JP); Hiroshi Kanai, Miyagi (JP); Hideyuki Hasegawa, Miyagi (JP)

(73) Assignee: Seiko Epson Corporation, Tokyo (JP)

( * ) Notice: Subject to any disclaimer, the term of this patent is extended or adjusted under 35 U.S.C. 154(b) by 373 days.

(21) Appl. No.: 14/290,443

(22) Filed: May 29, 2014

(65) Prior Publication Data
US 2014/0352437 A1 Dec. 4, 2014

(30) Foreign Application Priority Data

May 31, 2013 (JP) ................................ 2013-116175

(51) Int. Cl.
*G06K 9/00* (2006.01)
*G01N 29/11* (2006.01)
(Continued)

(52) U.S. Cl.
CPC ............. *G01N 29/11* (2013.01); *A61B 8/4483* (2013.01); *A61B 8/4494* (2013.01); *G01N 29/4472* (2013.01); *G01N 29/46* (2013.01); *G01N 29/52* (2013.01); *A61B 8/4405* (2013.01); *A61B 8/4427* (2013.01); *G01N 2291/02475* (2013.01); *G01N 2291/044* (2013.01)

(58) Field of Classification Search
None
See application file for complete search history.

(56) References Cited

U.S. PATENT DOCUMENTS

| 4,561,019 A | 12/1985 | Lizzi et al. | |
|---|---|---|---|
| 2009/0082669 A1* | 3/2009 | Kakee .................... | A61B 8/14 600/443 |

(Continued)

FOREIGN PATENT DOCUMENTS

| JP | 01-212543 | * 8/1989 | ............... A61B 8/14 |
|---|---|---|---|
| JP | 01-212543 A | 8/1989 | |

(Continued)

OTHER PUBLICATIONS

Kageyama et al; "Increasing Bandwidth of Ultrasound Radio Frequency Echoes Using Wiener Filter for Improvement of Accuracy in Measurement of Intima-Media Thickness"; Japanese Journal of Applied Physics 52; Jun. 2013; pp. 1-7.*

(Continued)

*Primary Examiner* — Amara Abdi
(74) *Attorney, Agent, or Firm* — Global IP Counselors, LLP

(57) ABSTRACT

An ultrasonic measuring device including: an ultrasonic transducer device; an emission unit for emitting an ultrasonic beam; a reception unit for receiving an ultrasonic echo reflected by a test subject; and a processing unit for processing reception, wherein the processing unit identifies a transfer function with respect to the ultrasonic transducer device and the test subject based on a first reception signal corresponding to an ultrasonic beam radiated to a first area in the test subject, a second reception signal corresponding to an ultrasonic beam radiated to a second area in the test subject, and a third reception signal corresponding to an ultrasonic beam radiated to a third area located between the first area and the second area in the test subject, and performs ultrasonic image generation processing including filter processing using a deconvolution filter including the transfer function performed on the reception signals.

20 Claims, 13 Drawing Sheets

(51) Int. Cl.
G01N 29/44 (2006.01)
G01N 29/46 (2006.01)
G01N 29/52 (2006.01)
A61B 8/00 (2006.01)

(56) References Cited

U.S. PATENT DOCUMENTS

| | | | | |
|---|---|---|---|---|
| 2009/0299186 | A1* | 12/2009 | Waters | A61B 5/02007 600/449 |
| 2012/0130247 | A1* | 5/2012 | Waters | A61B 5/02007 600/449 |
| 2012/0209119 | A1* | 8/2012 | Ohshima | A61B 8/4477 600/443 |
| 2012/0281902 | A1* | 11/2012 | Oikawa | G01S 7/52034 382/131 |

FOREIGN PATENT DOCUMENTS

| | | |
|---|---|---|
| JP | 2011-521730 A | 7/2011 |
| WO | 2009/146414 A1 | 12/2009 |

OTHER PUBLICATIONS

Kageyama et al.; Increasing Bandwidth of Ultrasound Radio Frequency Echoes Using Wiener Filter for Improvement of Accuracy in Measurement of Intima-Media Thickness; Japanese Journal of Applied Physics 52; Jun. 2013; pp. 07HF04-1 to 07HF04-7.

Sho et al.; Arterial Enlargement in Response to High Flow Requires Early Expression of Matrix Metalloproteinases to Degrade Extracellular Matrix; Experimental and Molecular Pathology 73; 2002; pp. 142-153.

Kitamura et al.; Accurate Estimation of Carotid Luminal Surface Roughness Using Ultrasonic Radio-Frequency Echo; Japanese Journal of Applied Physics 51; Jul. 2012; pp. 07GH0801 to 07GH08-12.

Ibrahim et al.; Detection of Boundaries of Carotid Arterial Wall by Analyzing Ultrasonic RF Signals; Japanese Journal of Applied Physiscs 51; Jul. 2012; pp. 07GF07-1 to 07GF07-8.

Arihara et al.; Accurate Ultrasonic Measurement of Surface Profile Using Phase Shift of Echo and Inverse Filtering; Japanese Journal of Applied Physics; May 2006; vol. 45 No. 5B, pp. 4727-4731.

Kimura et al.; High-Resolution Determination of Transit Time of Ultrasound in a Thin Layer in Pulse-Echo Method; IEICE Trans. Fundamentals, vol. E78-A, No. 12; Dec. 1995; pp. 1677-1682.

Huber et al.; Real-time Spatial Compound Imaging in Breast Ultrasound; Ultrasound in Med. & Biol., vol. 28, No. 2 pp. 155-163; 2002.

Pernot et al.; Temperature Estimation Using Ultrasonic Spatial Compound Imaging; IEEE Transactions on Ultrasonics, Ferroelectrics, and Frequency Control, vol. 51, No. 5, May 2004; pp. 606-615.

Sanchez et al.; An Ultrasonic Imaging Speckle-Suppression and Contrast-Enhancement Technique by Means of Frequency Compounding and Cded Excitation; IEEE Transactions on Ultrasonics, Ferroelectrics, and Frequency Control, vol. 56, No. 7, Jul. 2009; pp. 1327-1339.

Magnin et al.; Frequency Compounding for Speckle Contrast Reduction in Phased Array Images; Ultrasonic Imaging 4, 1982; pp. 267-281.

Trahey et al.; A Quantitative Approach to Speckle Reduction via Frequency Compounding; Ultrasonic Imaging 8, 1986; pp. 151-164.

Akiyama et al.; Multiple-Frequency Ultrasonic Imaging Using a Multiple-Resonance Transducer; IEEE International Ultrasonic Symposium Proceedings; 2009; pp. 2712-2717.

Abbott et al.; Acoustic Speckle; Theory and Experimental Analysis; Ultrasonic Imaging 1; 1979; pp. 303-324.

Gehlbach et al.; Frequency Diversity Speckle Processing; Ultrasonic Imaging 9; 1987; pp. 92-105.

Melton et al.; A-Mode Speckle Reduction with Compound Frequencies and Compound Bandwidths; Ultrasonic Imaging 6, 1984; pp. 159-173.

Newhouse et al.; Flaw-to-grain Echo Enhancement by Split-spectrum Processing; Ultrasonics Imaging 20; Mar. 1982; pp. 59-68.

Yoshizumi et al.; Multiple-frequency Ultrasonic Imaging by Transmitting U;Ised Waves of Two Frequencies; J Med Ultrasonics; 2009; pp. 53-60.

Rosenfeld et al.; Dijitaru Gazo Shori (Digital Image Processing); Kindai Kagaku, Tokyo, 1978.

Pratt; Digital Image Processing; Wiley, New York; 1978.

Andrew et al.; Digital Image Restoration; Prentice Hall, Upper Saddle River, NJ, 1997; pp. 147-153.

Saito; Dijitaru Gazo Shori (Digial Image Processing); Tokai University Press, Hiratsuka; 1986.

Jan; Medical Image Processing, Reconstruction and Restoration; Concepts and Methods; CRC Press, Boca Raton, FL; 2005; pp. 561-575.

Kanai; Oto to Shindo no Supekutoru Kaiseki (Spectrum Analysis of Sound and Vibration); Corona, Tokyo; 2008.

Fukushima et al.; Estimation of Scatterer Diameter by Normalized Power Spectrum of High-Frequency Ultrasonic FR Echo for Assessment of Red Blood Cell Aggregation; Japanese Journal of Applied Physics 50; Jul. 2011; pp. 07HF02-1 to 07HF02-8.

Taxt et al.; Superresolution of Ultrasound Images Using the First and Second Harmonic Signal; IEEE Transactions on Ultrasonics, and Frequency Control, vol. 51, No. 2; Feb. 2004; pp. 163-175.

Iraca et al.; Power Spectrum Equalization for Ultrasonic Image Restoration; IEEE Transactions on Ultrasonics, Ferroelectrics, and Frequency Control, vol. 36, No. 2; Mar. 1989; pp. 216-222.

Yeoh et al.; Constrained Least Squares Filtering Algorithm for Ultrasound Image Deconvolution; IEEE Transactions on Biomedical Engineering; vol. 53, Nov. 10; Oct. 2006; pp. 2001-2007.

Sin et al.; A Comparison of Deconvolution Techniques for the Ultrasonic Nondestructive Evaluation of Materials; IEEE Transactions on Image Processing, vol. 1, No. 1; Jan. 1992; pp. 3-10.

Masoy et al.; Correction of Ultrasonic Wave Aberration with a Time Delay and Amplitude Filter; J. Acoust. Soc. Am. 113 (4) Pt. 1; Apr. 2003; pp. 2009-2020.

Hantscher et al.; Ultra-wideband Radar Noise Reduction for Target Classification; IET Radar Sonar Navig. 2008, vol. 2, No. 4; pp. 315-322.

Fienup et al.; Comparison of Reconstruction Algorithms for Images from Sparse-Aperture Systems; Proc. SPIE 4792-01, Image Reconstruction from Incomplete Data II, Seattle, WA; Jul. 2002.

* cited by examiner

ULTRASONIC MEASURING DEVICE, ULTRASONIC IMAGE DEVICE, AND METHOD FOR PROCESSING ULTRASONIC IMAGE

BACKGROUND

1. Technical Field

The present invention relates to an ultrasonic measuring device, an ultrasonic image device, and a method for processing an ultrasonic image, and the like.

2. Related Art

Ultrasonic diagnostic devices have a problem in that a signal obtained by emitting ultrasound from an ultrasonic transducer and receiving the ultrasound reflected by a target subject by the ultrasonic transducer convolves narrow band characteristics of the ultrasonic transducer, and thus the reflected signal has a wide pulse width even if the target subject is a spot, resulting in an ultrasonic image in which the target subject appears stretched.

To address this problem, in order to improve the resolution of ultrasonic images, a technique is known for obtaining an ultrasonic image having a high spatial resolution by removing the narrow band characteristics of the ultrasonic transducer convolved in the reception signal with the use of a filter (deconvolution filter) so as to reduce spreading of the reception signal.

For example, JP-A-2011-521730 discloses a technique in which in order to remove a dip included in a power spectrum of the reception signal when determining a transfer function with respect to individual scan lines, a cepstrum of the power spectrum is determined, and only a low frequency component is extracted therefrom. This method, however, requires a significant amount of calculation time and memory, and also has a problem in that the spreading of the reception signal cannot be reduced to a satisfactory level because phase characteristics are not included in the transfer function.

SUMMARY

An advantage of some aspects of the invention is to provide an ultrasonic measuring device, an ultrasonic image device, a method for processing an ultrasonic image, and the like that can efficiently generate an ultrasonic image having a high spatial resolution.

A first aspect of the invention relates to an ultrasonic measuring device including: an ultrasonic transducer device; an emission unit that performs processing for emitting an ultrasonic beam; a reception unit that performs processing for receiving an ultrasonic echo, which is obtained as a result of the ultrasonic beam being reflected by a test subject; and a processing unit that performs processing based on reception signals from the reception unit, wherein the processing unit identifies a transfer function with respect to the ultrasonic transducer device and the test subject based on a first reception signal corresponding to an ultrasonic echo of an ultrasonic beam radiated to a first area in the test subject, a second reception signal corresponding to an ultrasonic echo of an ultrasonic beam radiated to a second area in the test subject, and a third reception signal corresponding to an ultrasonic echo of an ultrasonic beam radiated to a third area in the test subject, the third area being located between the first area and the second area, and performs ultrasonic image generation processing including filter processing using a deconvolution filter including the transfer function performed on the reception signals.

According to this aspect of the invention, the processing unit can identify a transfer function of the ultrasonic transducer device and the test subject based on the first, second and third reception signals, and it is therefore possible to perform highly accurate filter processing using a deconvolution filter in a short processing time. As a result, an ultrasonic image having a high spatial resolution can be efficiently generated. The reception signal to be subjected to the filter processing is a reception signal used to generate an ultrasonic image. The reception signal may include the first, second and third reception signals, or may not include them.

Also, in the first aspect of the invention, the processing unit may obtain a first power spectrum of the first reception signal, a second power spectrum of the second reception signal, and a third power spectrum of the third reception signal, and determine an amplitude of the transfer function from the first power spectrum, the second power spectrum, and the third power spectrum.

According to this configuration, the processing unit can determine the amplitude of the transfer function of the ultrasonic transducer device and the test subject in a short processing time.

Also, in the first aspect of the invention, a characteristics information storage unit that stores information regarding phase characteristics of a transfer function with respect to the ultrasonic transducer device may be included, and the processing unit may perform the filter processing using a deconvolution filter by using the information regarding phase characteristics of the transfer function with respect to the ultrasonic transducer device stored in the characteristics information storage unit, and the amplitude of the transfer function determined from the first reception signal, the second reception signal, and the third reception signal.

According to this configuration, the processing unit can perform the filter processing using a deconvolution filter by using the transfer function that includes both the amplitude and the phase characteristics. It is therefore possible to generate a more highly accurate ultrasonic image.

Also, in the first aspect of the invention, it is possible that $M(\omega)=H^*(\omega)/(|H(\omega)|^2+\beta \times Pn(\omega)/Pf(\omega))$, where $\omega$ represents an angular frequency, $|H(\omega)|$ represents the amplitude of the transfer function, $H^*(\omega)$ represents a complex conjugate of the transfer function, $Pn(\omega)$ represents a power spectrum of noise components of the reception signals, $Pf(\omega)$ represents a power spectrum of signal components of the reception signals, $\beta$ represents an adjustment factor value, and $M(\omega)$ represents the deconvolution filter.

According to this configuration, the processing unit can perform filter processing by using the deconvolution filter $M(\omega)$.

Also, in the first aspect of the invention, the characteristics information storage unit may further store the adjustment factor value $\beta$, and the processing unit may perform the filter processing using a deconvolution filter by using the adjustment factor value $\beta$ stored in the characteristics information storage unit.

According to this configuration, the characteristics information storage unit can store an adjustment factor value $\beta$ determined through, for example, ultrasonic measurement performed under water. Then, the processing unit can perform the filter processing using a deconvolution filter by using the adjustment factor value $\beta$ stored in the characteristics information storage unit.

Also, in the first aspect of the invention, the characteristics information storage unit may store, as the adjustment factor value $\beta$, different values depending on the ultrasonic transducer device or the test subject.

According to this configuration, the characteristics information storage unit can store an adjustment factor value β determined for each ultrasonic transducer device, or an adjustment factor value β determined for each test subject.

Also, in the first aspect of the invention, the processing unit may perform the filter processing using a deconvolution filter by using the adjustment factor value β that varies depending on the ultrasonic transducer device or the test subject.

According to this configuration, the processing unit can perform the filter processing using a deconvolution filter by using a different adjustment factor value β according to the ultrasonic transducer device or the test subject, and it is therefore possible to generate a more highly accurate ultrasonic image.

Also, in the first aspect of the invention, the adjustment factor value β may be 0.2 or less.

According to this configuration, the processing unit can generate an ultrasonic image having a high spatial resolution while suppressing amplification of noise.

Also, in the first aspect of the invention, an input receiving unit that receives input of information regarding the adjustment factor value β may be included, and the processing unit may perform the filter processing using a deconvolution filter by using the information regarding the adjustment factor value β received by the input receiving unit.

According to this configuration, the processing unit can perform the filter processing using a deconvolution filter by using an adjustment factor value β input by the user.

Also, in the first aspect of the invention, the processing unit may determine the power spectrum $Pf(\omega)$ of the signal components based on time average values of power spectra of a plurality of reception signals measured at different time instants, and determine the power spectrum $Pn(\omega)$ of the noise components based on variances of the power spectra of the plurality of reception signals measured at the different time instants.

According to this configuration, the processing unit can determine the power spectrum $Pf(\omega)$ of signal components and the power spectrum $Pn(\omega)$ of noise components in a short processing time, and it is therefore possible to efficiently generate an ultrasonic image having a high spatial resolution.

Also, in the first aspect of the invention, the processing unit may identify a first transfer function to an n-th transfer function with respect to a first area to an n-th area (where n is an integer of 2 or greater) that have different depths in the test subject, and perform the filter processing by using a first deconvolution filter to an n-th deconvolution filter including the first transfer function to the n-th transfer function with respect to the first area to the n-th area.

According to this configuration, the processing unit can perform filter processing by using a deconvolution filter corresponding to each of a plurality of areas having different depths in the test subject, and it is therefore possible to generate an ultrasonic image having a higher spatial resolution.

Also, in the first aspect of the invention, the first area in the test subject may be an area corresponding to a first edge of the ultrasonic image, the second area in the test subject may be an area corresponding to a second edge of the ultrasonic image that is located opposite to the first edge, and the third area in the test subject may be an area located between the first edge and the second edge in the ultrasonic image.

According to this configuration, the processing unit can identify the transfer function based on reception signals of ultrasonic echoes from areas corresponding to two edges of the ultrasonic image and the center between the two edges.

Another aspect of the invention relates to an ultrasonic image device including: any one of the above-described ultrasonic measuring devices; and a display unit that displays the ultrasonic image.

Another aspect of the invention relates to an ultrasonic image processing method executed by a processing unit of an ultrasonic measuring device including: an ultrasonic transducer device; an emission unit that performs processing for emitting an ultrasonic beam; a reception unit that performs processing for receiving an ultrasonic echo, which is obtained as a result of the ultrasonic beam being reflected by a test subject; and the processing unit that performs processing based on reception signals from the reception unit, the method including: identifying a transfer function with respect to the ultrasonic transducer device and the test subject based on a first reception signal corresponding to an ultrasonic echo of an ultrasonic beam radiated to a first area in the test subject, a second reception signal corresponding to an ultrasonic echo of an ultrasonic beam radiated to a second area in the test subject, and a third reception signal corresponding to an ultrasonic echo of an ultrasonic beam radiated to a third area in the test subject, the third area being located between the first area and the second area, and performing filter processing using a deconvolution filter including the transfer function on the reception signals.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following is a detailed description of preferred embodiments of the invention. Note that the embodiments described below are not intended to unduly limit the content of the invention recited in the claims, and all of the configurations described in the embodiments are not necessarily essential as solutions provided by the invention.

1. Basic Configuration Example of Ultrasonic Measuring Device

Figure 1:
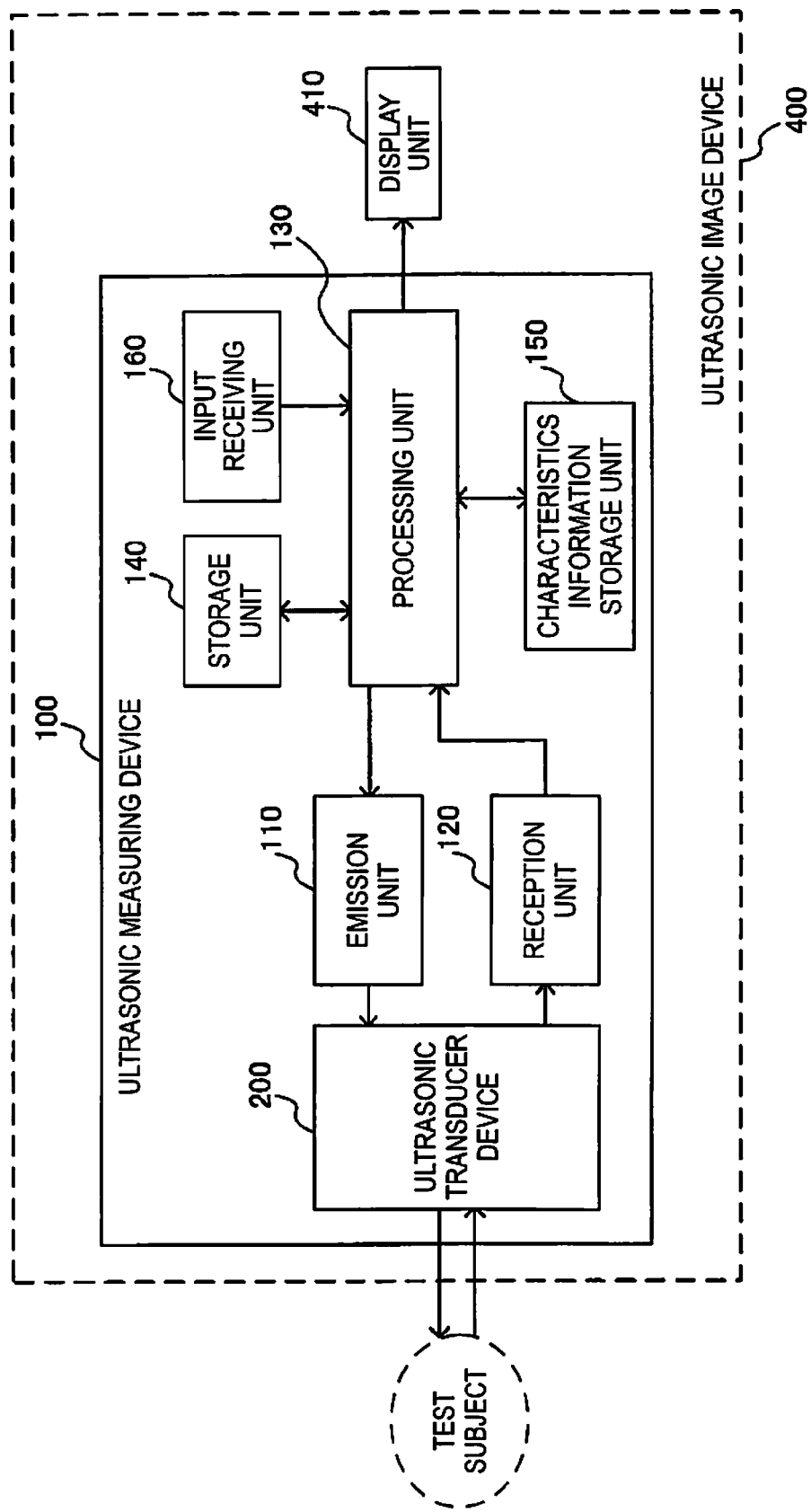
FIG. 1 shows an example of basic configurations of an ultrasonic measuring device and an ultrasonic image device.

FIG. 1 shows an example of the basic configurations of an ultrasonic measuring device 100 and an ultrasonic image device 400 of this embodiment. The ultrasonic measuring device 100 of this embodiment includes an ultrasonic transducer device 200, an emission unit 110, a reception unit 120, a processing unit 130, a storage unit 140, a characteristics information storage unit 150, and an input receiving unit 160. The ultrasonic image device 400 includes the ultrasonic measuring device 100 and a display unit 410. Note that the ultrasonic measuring device 100 and the ultrasonic image device 400 of this embodiment are not limited to the configurations shown in FIG. 1, and various modifications can be carried out, such as omitting some of the constituent elements, replacing some of the constituent elements with other constituent elements, and adding other constituent elements.

The ultrasonic transducer device 200 includes ultrasonic transducer elements. The ultrasonic transducer elements convert an emission signal, which is an electrical signal, into ultrasound, and convert an ultrasonic echo from a target subject (test subject) into an electrical signal. The ultrasonic transducer elements may be thin-film piezoelectric ultrasonic transducer elements, bulk piezoelectric ultrasonic transducer elements, CMUT (Capacitive Micromachined Ultrasonic Transducer) elements, or the like.

The emission unit 110 performs processing for emitting an ultrasonic beam. Specifically, the emission unit 110 outputs an emission signal (drive signal), which is an electrical signal, to the ultrasonic transducer device 200 under control of the processing unit 130, and the ultrasonic transducer device 200 converts the emission signal, which is an electrical signal, into ultrasound and emits the ultrasound.

The reception unit 120 performs processing for receiving an ultrasonic echo obtained from an ultrasonic beam being reflected by the test subject. Specifically, the ultrasonic transducer device 200 converts an ultrasonic echo from the target subject into an electrical signal, and outputs the electrical signal to the reception unit 120. The reception unit 120 performs reception processing, such as amplification, wave detection, A/D conversion and phase alignment, on a reception signal (analog signal), which is the electrical signal transmitted from the ultrasonic transducer device 200, and outputs the reception signal (digital data), which is a signal obtained as a result of the reception processing, to the processing unit 130.

The processing unit 130 performs processing for controlling the emission unit 110 and the reception unit 120, and processing for generating an ultrasonic image based on reception signals from the reception unit 120. Specifically, the processing unit 130 performs, on the reception signals, frequency analysis processing, filter processing using a deconvolution filter, absolute value processing, envelope detection processing, intensity modulation processing, and the like. The deconvolution filter will be described later in detail.

The processing unit 130 may be configured by, for example, a dedicated digital signal processor (DSP), or a general-purpose microprocessing unit (MPU). Alternatively, a part of processing executed by the processing unit 130 may be executed by a personal computer (PC).

The storage unit 140 is configured by, for example, a storage device such as, for example, a DRAM, and stores information regarding the amplitude of a transfer function identified based on reception signals and the power spectra of the reception signals. The information regarding the amplitude of a transfer function refers to information that can identify the amplitude of the transfer function, and may be, for example, a table or function that indicates the relationship between the amplitude of the transfer function and frequency, or a parameter.

The characteristics information storage unit 150 is configured by, for example, a nonvolatile storage device such as a flash memory, and stores information regarding the phase characteristics of the transfer function of the ultrasonic transducer device 200, and information regarding an adjustment factor value $\beta$ included in the deconvolution filter. The information regarding the phase characteristics of the transfer function refers to information that can identify the phase characteristics of the transfer function, and may be, for example, a table or function that indicates the relationship between phase and frequency, or a parameter that determines the phase characteristics. The information regarding the adjustment factor value $\beta$ refers to information that can identify an adjustment factor value $\beta$, and may be, for example, an adjustment factor value $\beta$ itself, or a function or parameter for determining the adjustment factor value $\beta$.

As will be described later, the phase characteristics of the transfer function and the adjustment factor value $\beta$ can be determined by ultrasonic measurement performed on a wire (point scatterer) under water. The phase characteristics of the transfer function and the adjustment factor value $\beta$ that have been determined may be stored in the characteristics information storage unit 150. Also, the characteristics information storage unit 150 may store, as the adjustment factor value $\beta$, different values for different ultrasonic transducer devices 200 or test subjects. The processing unit 130 may perform filter processing using a deconvolution filter by using the adjustment factor value $\beta$ that differs for each ultrasonic transducer device 200 or test subject. As used herein, the expression "differ for each test subject" encompasses a case in which the value varies depending on, for example, the measurement site in the human body subjected to measurement.

The input receiving unit 160 is an input device such as a keyboard or a touch panel, and receives an adjustment factor value $\beta$ input by the user. The processing unit 130 can perform filter processing with a deconvolution filter by using the adjustment factor value $\beta$ received by the input receiving unit 160.

The display unit 410 is a display device such as a liquid crystal display, and displays an ultrasonic image (for example, B mode image) generated by the processing unit 130.

2. Identification of Transfer Function

Figure 2A:
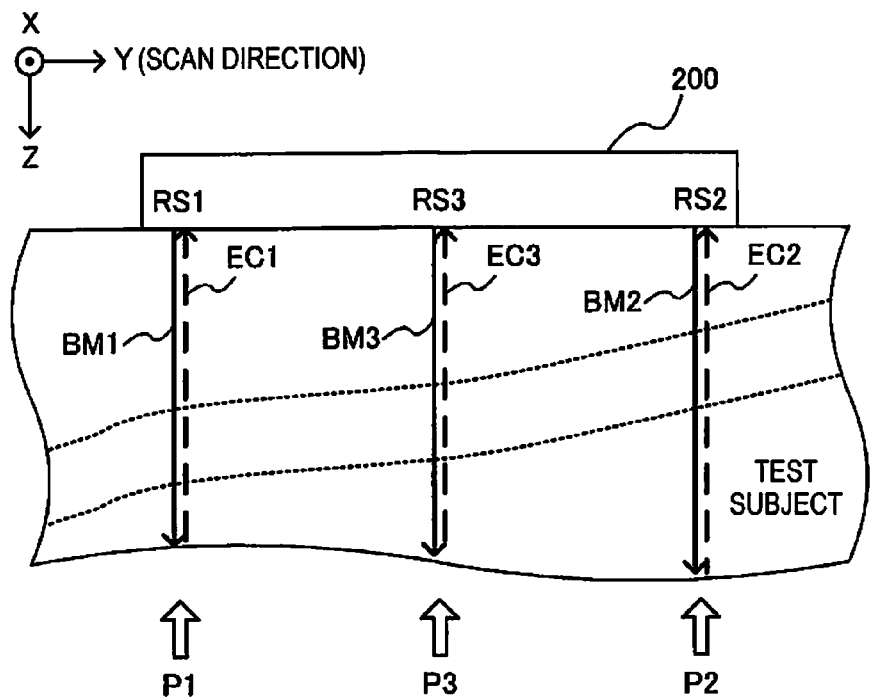
FIGS. 2A and 2B are diagrams illustrating first, second and third reception signals for determining an amplitude of a transfer function.
Figure 2B:
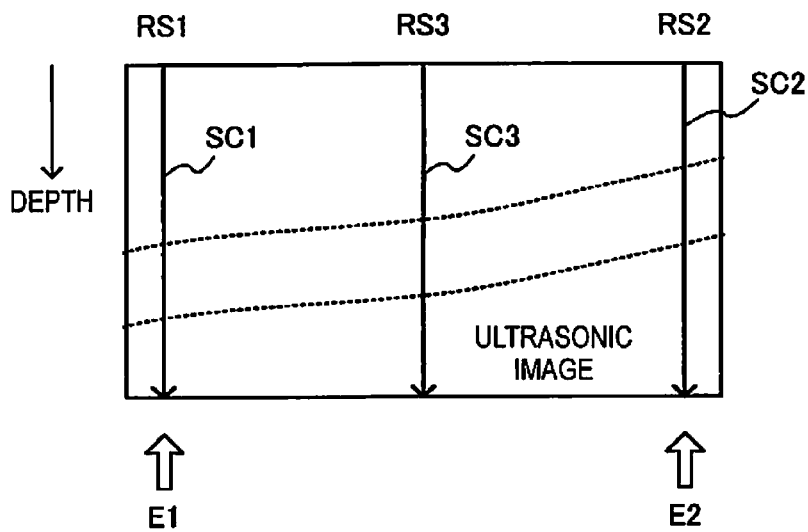

A description will be given of identification of the amplitude of a transfer function in a first configuration example of the ultrasonic measuring device 100 of this embodiment. FIGS. 2A and 2B are diagrams illustrating a first reception signal, a second reception signal and a third reception signal for determining the amplitude of a transfer function. As shown in FIG. 2A, a first reception signal RS1 is a reception signal corresponding to an ultrasonic echo EC1 of an ultrasonic beam BM1 radiated to a first area P1 of a test subject. The first area P1 of the test subject is, as shown in FIG. 2B, an area corresponding to a first edge E1 of an ultrasonic image (one frame image). That is, the first reception signal RS1 is a reception signal corresponding to a single scan line SC1 located in the first edge E1 of the ultrasonic image.

The edge of an ultrasonic image refers to an area where scanning with ultrasonic beams starts or ends in one frame of ultrasonic image (for example, B mode image), and includes a plurality of scan lines. Each scan line is a collection of pixels arranged along a single straight line extending in a depth direction in one frame of ultrasonic image. The single scan line SC1 located in the first edge E1 of the ultrasonic image does not necessarily need to be the leftmost scan line in, for example, FIG. 2A, and may be one of a plurality of scan lines located in the first edge E1.

Likewise, a second reception signal RS2 is a reception signal corresponding to an ultrasonic echo EC2 of an ultrasonic beam BM2 radiated to a second area P2 of the test subject. The second area P2 of the test subject is an area corresponding to a second edge E2 of the ultrasonic image, which is located opposite to the first edge E1. That is, the second reception signal RS2 is a reception signal corresponding to a single scan line SC2 located in the second edge E2 of the ultrasonic image.

A third reception signal RS3 is a reception signal corresponding to an ultrasonic echo EC3 of an ultrasonic beam BM3 radiated to a third area P3 between the first area P1 and the second area P2 of the test subject. The third area P3 of the test subject is an area that is located between the first edge E1 and the second edge E2 of the ultrasonic image. That is, the third reception signal RS3 is a reception signal corresponding to a single scan line (for example, a scan line at the center in the ultrasonic image) SC3 located between the first edge E1 and the second edge E2 of the ultrasonic image.

The processing unit 130 determines the amplitude of a transfer function from the first, second and third reception signals in the following manner.

The processing unit 130 performs frequency analysis on the first, second and third reception signals RS1, RS2 and RS3 so as to obtain a first power spectrum, a second power spectrum and a third power spectrum. Then, from the first, second and third power spectra, the amplitude of a transfer function is determined with respect to the ultrasonic transducer device 200 and the test subject. Specifically, the processing unit 130 averages the first, second and third power spectra, and defines the square root of the averaged power spectrum as the amplitude of the transfer function.

The foregoing stated that the first, second and third reception signals RS1, RS2 and RS3 are reception signals respectively corresponding to the scan lines SC1, SC2 and SC3 of the ultrasonic image, but they do not necessarily need to be reception signals corresponding to the scan lines of the ultrasonic image. For example, the first, second and third reception signals RS1, RS2 and RS3 may be A mode waveforms of ultrasonic echoes from the first, second and third areas P1, P2 and P3 of the test subject.

As the reception signals for determining the amplitude of a transfer function, it is possible to use four or more reception signals corresponding to ultrasonic echoes of ultrasonic beams radiated to four or more areas of the test subject. In this case, power spectra PS1(f) to PSn(f) of the first to n-th (where n is an integer of 4 or greater) reception signals RS1 to RSn are averaged, and the square root of the averaged power spectrum is defined as the amplitude $|H(f)|$ of the transfer function.

Figure 3A:
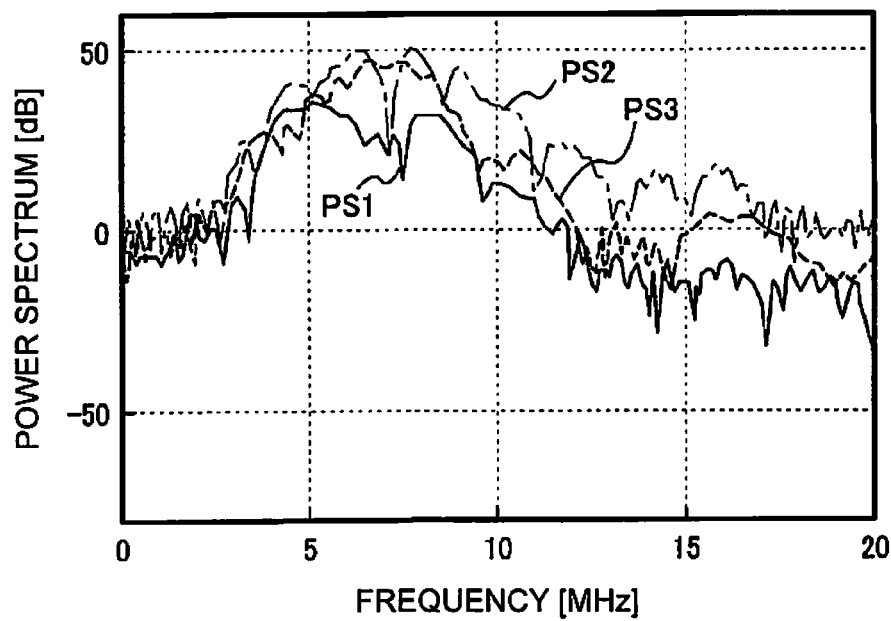
FIG. 3A shows an example of power spectra of the first, second and third reception signals.

FIG. 3A shows an example of the power spectra PS1(f), PS2(f) and PS3(f) of the first, second and third reception signals RS1, RS2 and RS3. Here, f represents frequency.

As can be seen from FIG. 3A, each of the power spectra PS1(f), PS2(f) and PS3(f) includes dips caused by interference of a plurality of reflected ultrasonic waves from the test subject. The frequency at which such a dip occurs depends on the positional relationship between a plurality of scatterers in the test subject. The scatterer arrangement varies depending on the measurement position, and thus the frequency at which a dip occurs also varies among the first, second and third reception signals RS1, RS2 and RS3. Accordingly, the first, second and third power spectra PS1(f), PS2(f) and PS3(f) are averaged, and the square root thereof is obtained so as to smooth the dips, and the amplitude of a desired transfer function, or in other words, an amplitude $|H(f)|$ of the transfer function of the ultrasonic transducer device 200 and the test subject is thereby obtained.

Figure 3B:
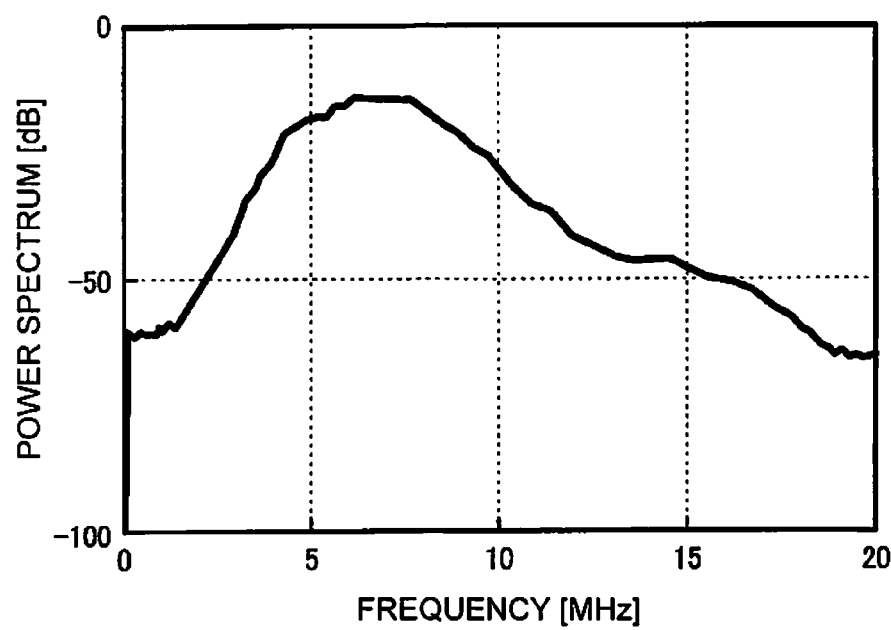
FIG. 3B shows an example of an amplitude of a transfer function determined from the first, second and third reception signals.

FIG. 3B shows an example of the amplitude $|H(f)|$ of the transfer function determined from the first, second and third reception signals RS1, RS2 and RS3. It can be seen from FIG. 3B that the dips are smoothened, and the influence of the dips is removed.

The amplitude $|H(f)|$ of the transfer function determined in the above-described manner represents not only the transfer characteristics of the ultrasonic transducer device 200, but also the transfer characteristics of the test subject (biological tissue). Accordingly, the amplitude $|H(f)|$ of the transfer function has characteristics that varies depending on the measurement site in the test subject. For this reason, in the actual ultrasonic measurement, the processing unit 130 determines the amplitude $|H(f)|$ of a transfer function corresponding to the measurement site in the test subject for each ultrasonic measurement, and performs filter processing using a deconvolution filter by using the amplitude $|H(f)|$ of the transfer function. By doing so, it is possible to obtain a highly accurate amplitude $|H(f)|$ that also includes transfer characteristics of the measurement site in the test subject.

Next is a description of identification of phase characteristics $\angle H(f)$ of the transfer function. The phase characteristics $\angle H(f)$ of the transfer function can be determined by ultrasonic measurement performed on a wire (point scatterer) under water. In the biological tissue, the amplitude of ultrasound attenuates depending on the frequency, but the phase characteristics are not so affected by attenuation that depends on the frequency, as compared to the amplitude. Accordingly, the phase characteristics of the transfer function of the ultrasonic transducer device measured under water can be regarded as the phase characteristics of the transfer function of the biological tissue.

Figure 4:
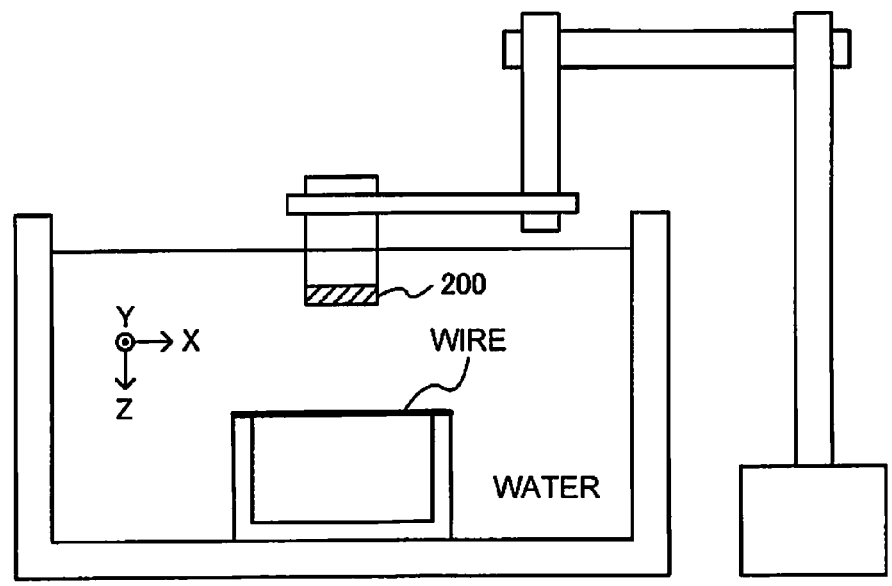
FIG. 4 shows an example of ultrasonic measurement performed on a wire under water.

FIG. 4 shows an example of ultrasonic measurement performed on a wire under water. As shown in FIG. 4, ultrasound is radiated from an ultrasonic transducer device 200 toward a wire having a small diameter (for example, a diameter of 13 µm) provided under water so as to perform ultrasonic measurement. The ultrasonic transducer device 200 is provided such that Y direction corresponds to the scan direction. The wire is provided so as to extend in X direction. Because ultrasonic beams are scanned in the Y direction, the wire can be regarded as a point scatterer.

Figure 5:
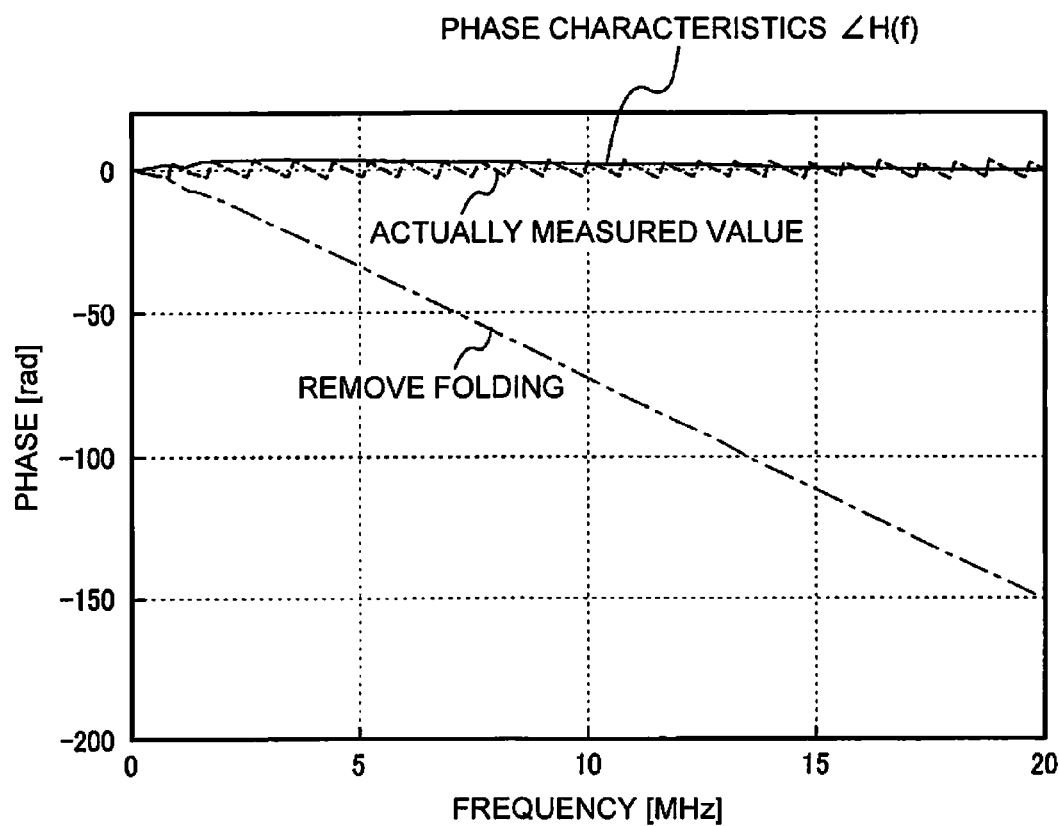
FIG. 5 shows an example of phase characteristics of the transfer function.

FIG. 5 shows an example of the phase characteristics $\angle H(f)$ of a transfer function determined through ultrasonic measurement performed on a wire under water. The broken line shown in FIG. 5 indicates actually measured phase data, from which it can be seen that folding has occurred. The dashed dotted line shown in FIG. 5 indicates phase data from which the influence of folding has been removed by unwrapping the phase. Furthermore, an amount of change in the phase due to propagation delay is removed, and thereby the phase characteristics ∠H(f) of a desired transfer function indicated by the solid line in FIG. 5 are obtained.

The phase characteristics ∠H(f) of the transfer function determined from the measurement performed under water as described above depend on the transfer characteristics of the ultrasonic transducer device 200. Accordingly, it is possible to determine in advance the phase characteristics ∠H(f) of the transfer function of each ultrasonic transducer device 200 through measurement performed under water and store the determined phase characteristics ∠H(f) in the characteristics information storage unit 150. By doing so, highly accurate phase characteristics ∠H(f) including variations in the characteristics of the ultrasonic transducer device 200 can be obtained.

With the ultrasonic measuring device 100 of this embodiment, the amplitude of the transfer function can be determined based on reception signals from at least three areas in the test subject. Furthermore, it is unnecessary to perform processing, such as determining a cepstrum so as to remove dips included in the power spectra of the reception signals, and thus the amplitude of the transfer function can be determined in a short processing time. Furthermore, the transfer function that also includes phase characteristics in addition to the amplitude can be used, and it is therefore possible to efficiently generate an ultrasonic image having a higher spatial resolution.

3. Deconvolution Filter

The ultrasonic measuring device 100 of this embodiment performs filter processing using a deconvolution filter by using the amplitude |H(f)| and the phase characteristics ∠H(f) of the transfer function determined in the above-described manner.

The deconvolution filter is, for example, a Wiener filter M(ω) as shown below.

[Math. 1]

$$M(\omega) = \frac{H(\omega)^*}{|H(\omega)|^2 + \beta \cdot Pn(\omega)/Pf(\omega)} \quad (1)$$

where ω represents an angular frequency, H*(ω) represents the complex conjugate of the transfer function H(ω), |H(ω)| represents the amplitude of the transfer function H(ω), Pn(ω) represents the power spectrum of noise components of reception signals, Pf(ω) represents the power spectrum of signal components of reception signals, and β represents an adjustment factor value.

Pn(ω)/Pf(ω) in Equation (1) corresponds to the inverse of an S/N (signal-to-noise ratio). That is, Pn(ω)/Pf(ω) becomes closer to 0 as the S/N becomes higher, and becomes closer to infinity as the S/N becomes lower. Accordingly, the Wiener filter M(ω) given by Equation (1) is as follows.

$$M(\omega) \rightarrow 1/H(\omega) \text{ (when the S/N is high)} \quad (2)$$

$$M(\omega) \rightarrow 0 \text{ (when the S/N is low)} \quad (3)$$

As can be seen from Expressions (2) and (3), the Wiener filter M(ω) efficiently works in a frequency region having a high S/N. That is, the Wiener filter M(ω) has the effect of suppressing amplification of noise.

Pf(ω) representing the power spectrum of signal components and Pn(ω) representing the power spectrum of noise components can be determined from two or more ultrasonic images (B mode images) measured at different time instants.

For example, with respect to each of single-frame images IM1, IM2 and IM3 measured respectively at time instants t1, t2 and t3, power spectra PS1(ω), PS2(ω) and PS3(ω) of reception signals corresponding to the first, second and third scan lines are obtained. Next, an average value of the power spectrum PS1(ω) obtained from the image IM1, the power spectrum PS1(ω) obtained from the image IM2, and the power spectrum PS1(ω) obtained from the image IM3 is obtained. That is, a time average value Av_PS1(ω) of the power spectra PS1(ω) at time instants t1, t2 and t3 is determined. In the same way, a time average value Av_PS2(ω) of the power spectra PS2(ω) at the time instants t1, t2 and t3, and a time average value Av_PS3(ω) of the power spectra PS3(ω) at the time instants t1, t2 and t3 is determined. Then, an average value of the three time average values Av_PS1(ω), Av_PS2(ω) and Av_PS3(ω) is obtained, which is defined as the power spectrum Pf(ω) of signal components.

Pn(ω) representing the power spectrum of noise components can be determined as follows. A variance Dp_PS1(ω) is determined with respect to the power spectra PS1(ω) at the time instants t1, t2 and t3. In the same way, variances Dp_PS2(ω) and Dp_PS2(ω) are determined with respect to the power spectra PS2(ω) and PS3(ω) at the time instants t1, t2 and t3. Then, an average value of the three variances Dp_PS1(ω), Dp_PS2(ω) and Dp_PS2(ω) is determined, which is defined as the power spectrum Pn(ω) of noise components.

In the single-frame images IM1, IM2 and IM3 measured at the time instants t1, t2 and t3, if the target subject or the ultrasonic probe is moving, the time average values Av_PS1(ω), Av_PS2(ω) and Av_PS3(ω) are not appropriately calculated. Accordingly, it is desirable to take measurement in a state in which the target subject or the ultrasonic probe is not moving. The state in which the target subject or the ultrasonic probe is not moving may be detected by using a tracking technique, or the movement of the target subject or the ultrasonic probe may be canceled.

In the foregoing, an example was described in which the power spectrum Pf(ω) of signal components and the power spectrum Pn(ω) of noise components are determined based on three images (frames) measured at different time instants, but the number of images is not limited to 3. The number of images (the number of frames) may be 2, or may be 4 or more as long as they are measured at different time instants.

The adjustment factor β is provided to adjust the degree of the effect of suppressing the amplification of noise. As can be seen from Equation (1), if the adjustment factor β takes a great value, the widening of bandwidth of the signal after filter processing is suppressed, and the amplification of noise is also suppressed. If, on the other hand, the adjustment factor β takes a small value, the widening of bandwidth of the signal after filter processing is prioritized, but noise is also amplified.

In the ultrasonic measuring device 100 of this embodiment, the adjustment factor β can be determined by performing ultrasonic measurement on a wire under water. Specifically, filter processing using a deconvolution filter (Wiener filter) is performed on the obtained reception signal by using the transfer function H(ω) of the ultrasonic transducer device 200 under water, the power spectrum Pn(ω) of noise components and the power spectrum $Pf(\omega)$ of signal components. Then, the adjustment factor $\beta$ is determined such that the half-value width of the amplitude of the processed signal be minimum. The adjustment factor value $\beta$ is, for example, 0.2 or less.

The characteristics information storage unit 150 can store adjustment factor values $\beta$ determined based on the results of measurement performed in advance under water. By doing so, the processing unit 130 can perform filter processing using a deconvolution filter by using an adjustment factor value $\beta$ stored in the characteristics information storage unit 150.

Also, the characteristics information storage unit 150 can store, as the adjustment factor value $\beta$, values that are different depending on the ultrasonic transducer device 200 or the test subject. By doing so, the processing unit 130 can perform filter processing using a deconvolution filter by using the adjustment factor value $\beta$ that varies depending on the ultrasonic transducer device 200 or the test subject.

Also, the processing unit 130 may perform filter processing using a deconvolution filter by using an adjustment factor value $\beta$ received by the input receiving unit 160. By doing so, the user can set the adjustment factor value $\beta$.

The deconvolution filter used in the ultrasonic measuring device 100 of this embodiment is not limited to the Wiener filter described above. It is also possible to use, for example, Lucy-Richardson method, a regularization filter, or the like.

Figure 6A:
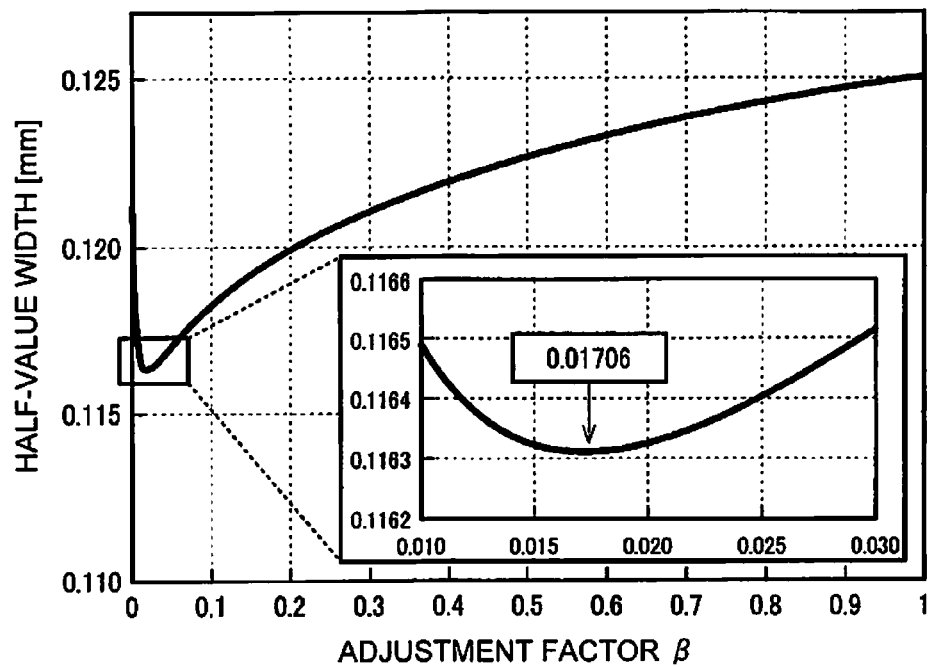
FIG. 6A shows an example of an adjustment factor β.
Figure 6B:
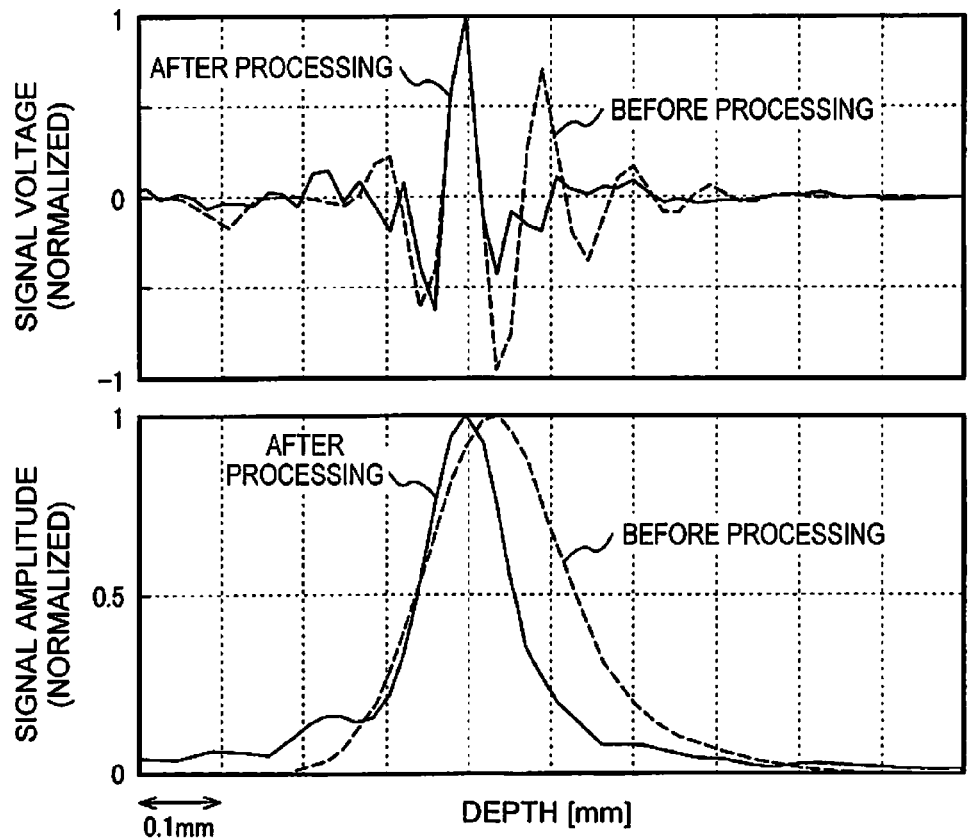
FIG. 6B shows signal voltage and half-value width before and after filter processing.

FIGS. 6A and 6B show an example of the adjustment factor $\beta$. FIG. 6A shows a relationship between the half-value width of the amplitude of the signal after filter processing and the adjustment factor $\beta$. FIG. 6B shows the signal voltage and the half-value width of the signal amplitude before and after filter processing.

As can be seen from FIG. 6A, the half-value width becomes smaller as the adjustment factor $\beta$ decreases, but when the adjustment factor $\beta$ takes a value that is too close to 0, the half-value width increases. In the example shown in FIG. 6A, the half-value width becomes minimum when the adjustment factor $\beta$ takes a value of 0.01706. Then, as shown in FIG. 6B, the half-value width of the amplitude of the signal after processing is reduced as compared to that before processing.

4. Flow of Filter Processing

A flow of filter processing using a deconvolution filter in the first configuration example of the ultrasonic measuring device 100 of this embodiment will be described. The flow of processing described below is executed by the processing unit 130. The processing unit 130 performs processing for determining a deconvolution filter as preliminary processing, and performs processing for performing filter processing on reception signals so as to generate image data based on the processed signals as main processing.

Figure 7:
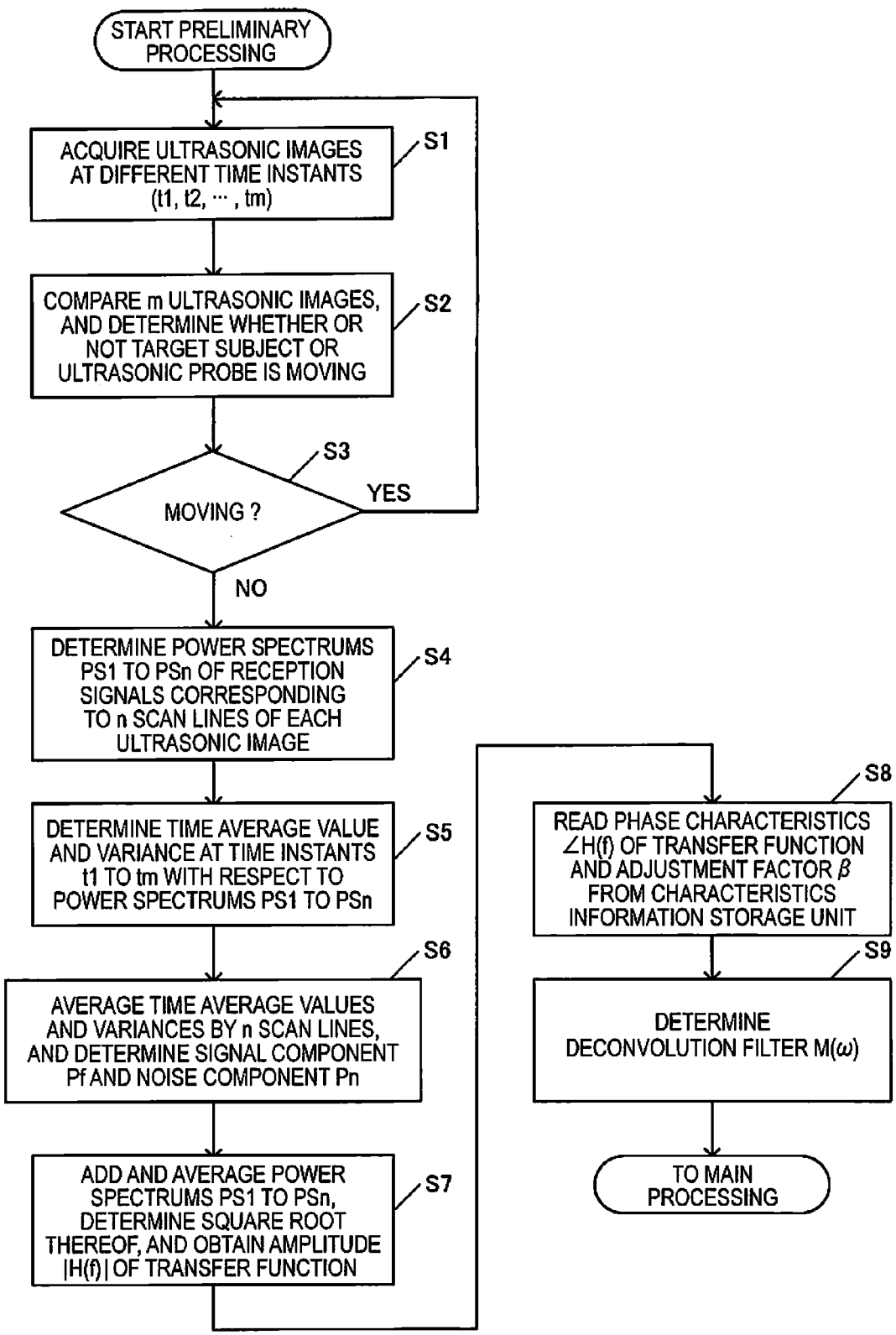
FIG. 7 shows an example of a flowchart of preliminary processing.

FIG. 7 shows an example of a flowchart of preliminary processing performed by the processing unit 130. First, the processing unit 130 performs ultrasonic measurement so as to acquire m ultrasonic images at different time instants t1, t2 . . . , and tm (where m is an integer of 2 or greater) (step S1). Next, the processing unit 130 makes comparison between the acquired m ultrasonic images, and determines whether or not the target subject or the ultrasonic probe is moving (steps S2 and S3). For example, the processing unit 130 can determine whether or not the target subject or the ultrasonic probe is moving by performing processing for extracting feature points from each of m ultrasonic images, and associating the extracted feature points. If the processing unit 130 determines that the target subject or the ultrasonic probe is moving, the procedure returns to step S1, where ultrasonic measurement is again performed. If the processing unit 130 determines that the target subject or the ultrasonic probe is not moving, the procedure advances to step S4.

In step S4, the processing unit 130 performs fast Fourier transformation on reception signals RS1 to RSn corresponding to n (where n is an integer of 3 or greater) scan lines of each ultrasonic image, so as to obtain power spectra PS1 to PSn. Next, with respect to the power spectra PS1 to PSn, the processing unit 130 determines the time average value and variance at the time instants t1 to tm (step S5). Then, the time average values and variances of the power spectra PS1 to PSn are averaged by n scan lines, thereby the power spectrum $Pf(\omega)$ of signal components and the power spectrum $Pn(\omega)$ of noise components are determined (step S6).

Next, the processing unit 130 averages the power spectra PS1 to PSn, and determines the square root thereof so as to obtain the amplitude $|H(f)|$ of a transfer function (step S7). Then, the processing unit 130 reads the phase characteristics $\angle H(f)$ of the transfer function and the adjustment factor $\beta$ from the characteristics information storage unit 150 (step S8). The processing unit 130 determines a deconvolution filter $M(\omega)$ by using the amplitude $|H(f)|$ of the transfer function determined as described above, and the phase characteristics $\angle H(f)$, the power spectrum $Pf(\omega)$ of signal components, the power spectrum $Pn(\omega)$ of noise components, and the adjustment factor $\beta$ (step S9).

The preliminary processing may be performed on each frame image, or may be performed on a plurality of frame images. In the case where the preliminary processing is performed on a plurality of frame images, filter processing is performed on reception signals corresponding to the plurality of frame images by using a deconvolution filter determined through the preliminary processing.

Figure 8:
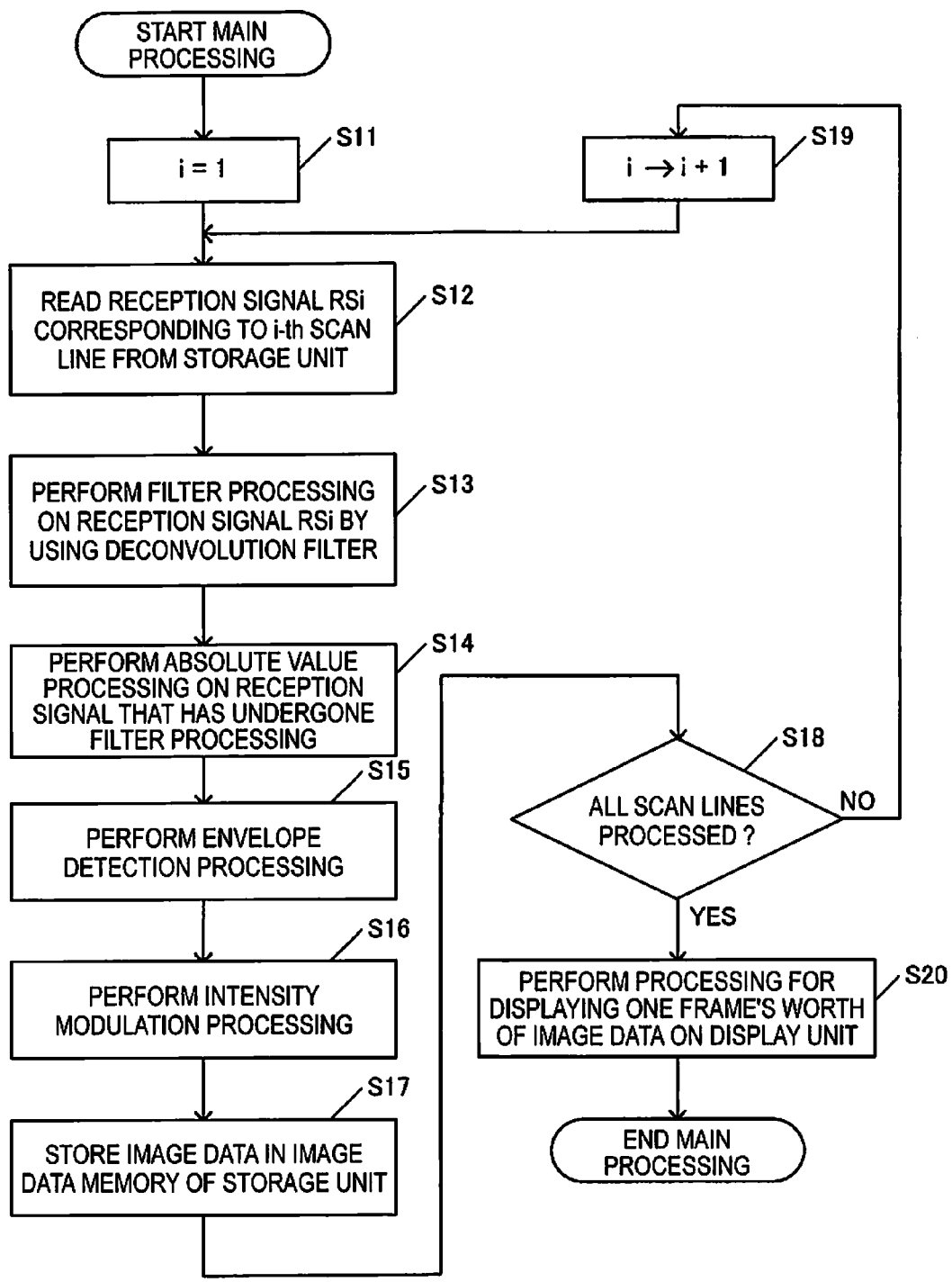
FIG. 8 shows an example of a flowchart of main processing.

FIG. 8 shows an example of a flowchart of main processing performed by the processing unit 130. First, the processing unit 130 sets a variable i representing the scan line number to an initial value of 1 (step S11). Next, the processing unit 130 reads a reception signal RSi corresponding to the measured i-th scan line from the storage unit 140 (step S12). Then, the processing unit 130 performs filter processing on the reception signal RSi by using the deconvolution filter $M(\omega)$ determined in the preliminary processing (step S13).

Next, the processing unit 130 performs absolute value processing on the reception signal that has undergone the filter processing (step S14), then performs envelope detection processing (step S15), and thereafter performs intensity modulation processing so as to generate image data corresponding to the i-th scan line (step S16). Then, the processing unit 130 stores the image data corresponding to the i-th scan line in a memory area corresponding to the i-th scan line in an image data memory in the storage unit 140 (step S17).

Next, the processing unit 130 determines whether or not all scan lines of the ultrasonic image have undergone filter processing and image data generation processing (step S18). If not all scan lines of the ultrasonic image have undergone filter processing and image data generation processing, the processing unit 130 increments the variable i (step S19), and performs processing on a reception signal corresponding to the next scan line (steps S12 to S17). If all scan lines of the ultrasonic image have undergone filter processing and image data generation processing, the processing unit 130 performs processing for displaying one frame's worth of image data on the display unit 410 (step S20).

Figure 9A:
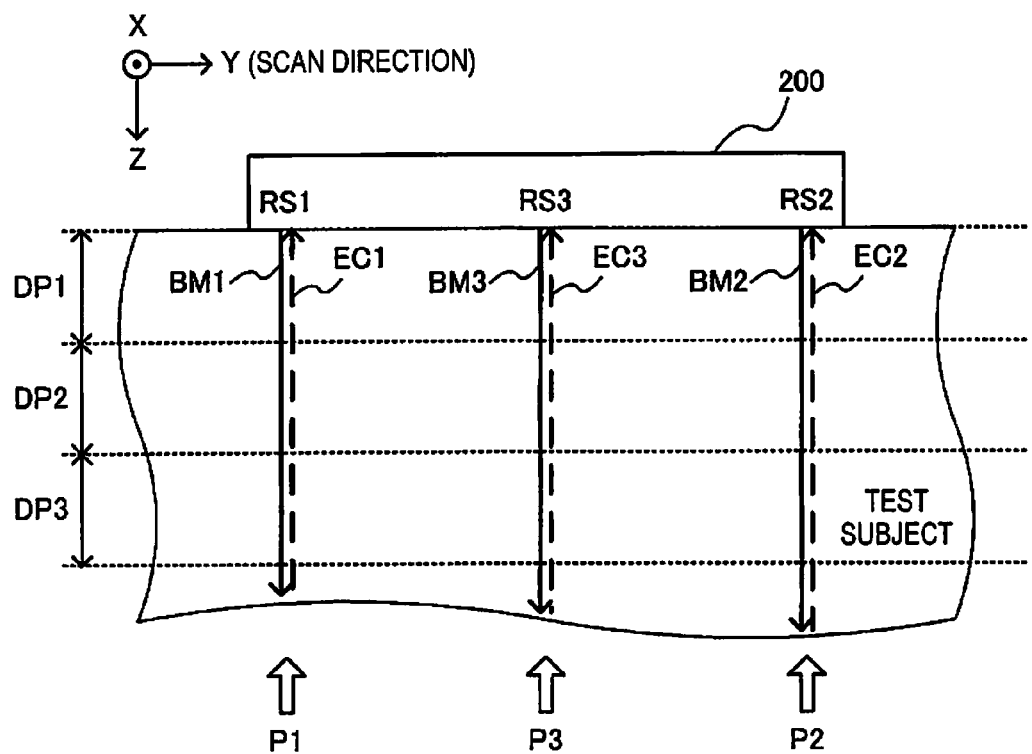
FIGS. 9A and 9B are diagrams illustrating identification of a transfer function according to a second configuration example of the ultrasonic measuring device.
Figure 9B:
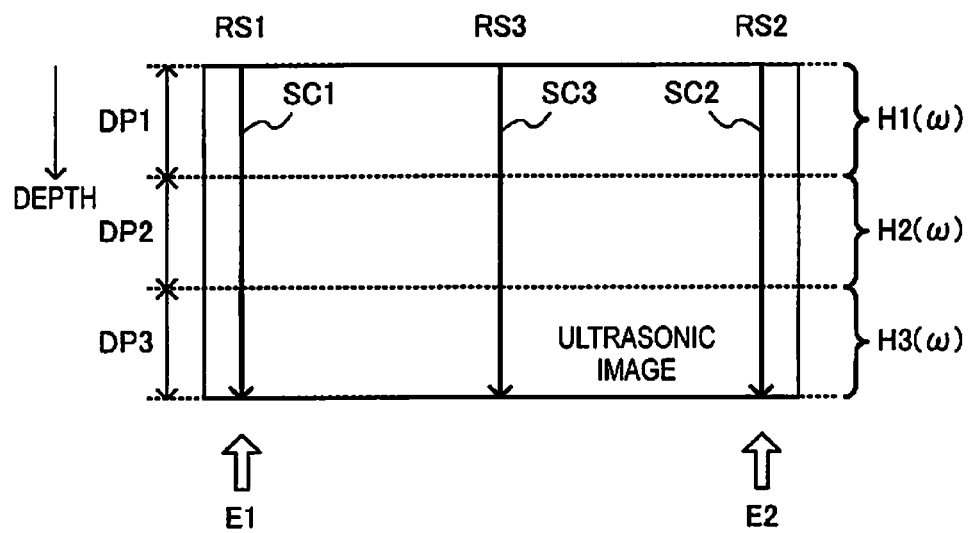

5. Identification of Transfer Function According to Second Configuration Example FIGS. 9A and 9B are diagrams illustrating identification of a transfer function in a second configuration example of the ultrasonic measuring device 100 of this embodiment. In the second configuration example, the processing unit 130 can identify first to n-th transfer functions $H1(\omega)$ to $Hn(\omega)$ corresponding to first to n-th areas DP1 to DPn (where n is an integer of 2 or greater) having different depths in the test subject. Then, filter processing is performed using first to n-th deconvolution filters $M1(\omega)$ to $Mn(\omega)$ corresponding to the first to n-th areas.

In FIGS. 9A and 9B, an example will be described in which first, second and third transfer functions $H1(\omega)$, $H2(\omega)$ and $H3(\omega)$ that correspond to first, second and third areas DP1, DP2 and DP3 having different depths in the test subject are identified.

FIG. 9A shows, as in FIG. 2A, ultrasonic beams BM1, BM2 and BM3 radiated to first, second and third areas P1, P2 and P3 in the test subject, and ultrasonic echoes EC1, EC2 and EC3 corresponding thereto. FIG. 9B shows, as in FIG. 2B, first, second and third scan lines SC1, SC2 and SC3 of one frame of ultrasonic image. First, second and third reception signals RS1, RS2 and RS3 are reception signals corresponding to the first, second and third scan lines SC1, SC2 and SC3 of the ultrasonic image.

The processing unit 130 performs frequency analysis on a time domain waveform corresponding to the first area DP1 among the first, second and third reception signals RS1, RS2 and RS3, so as to obtain power spectra PS1(f), PS2(f) and PS3(f). Then, the power spectra PS1(f), PS2(f) and PS3(f) are averaged, and the square root of the averaged power spectrum is defined as the amplitude |H1(f)| of the transfer function of the first area DP1.

Likewise, the processing unit 130 performs frequency analysis on a time domain waveform corresponding to the second area DP2 among the first, second and third reception signals RS1, RS2 and RS3, so as to obtain power spectra PS1(f), PS2(f) and PS3(f). Then, the power spectra PS1(f), PS2(f) and PS3(f) are averaged, and the square root of the averaged power spectrum is defined as the amplitude |H2(f)| of the transfer function of the second area DP2. The same processing is performed on the third area DP3, so as to obtain the amplitude |H3(f)| of the transfer function of the third area DP3.

The processing unit 130 performs filter processing by using deconvolution filters $M1(\omega)$, $M2(\omega)$ and $M3(\omega)$ including the transfer functions $H1(\omega)$, $H2(\omega)$ and $H3(\omega)$ identified in the manner described above. Specifically, with respect to the first area DP1, filter processing is performed using the first deconvolution filter $M1(\omega)$. With respect to the second area DP2, filter processing is performed using the second deconvolution filter $M2(\omega)$. With respect to the third area DP3, filter processing is performed using the third deconvolution filter $M3(\omega)$.

The processing unit 130 can determine the power spectrum $Pf(\omega)$ of signal components and the power spectrum $Pn(\omega)$ of noise components for each of the first, second and third areas DP1, DP2 and DP3. For example, the power spectrum $Pf(\omega)$ of signal components that corresponds to the first area DP1 can be determined from the power spectra of reception signals corresponding to the first area DP1 of two or more ultrasonic images measured at different time instants.

The reception signals to be subjected to filter processing are reception signals used to generate an ultrasonic image, and may include the reception signals RS1 to RSn measured in the preliminary processing, or may not include them.

In this way, with the second configuration example of the ultrasonic measuring device 100, filter processing can be performed by using a deconvolution filter corresponding to each of a plurality of areas having different depths in the test subject, and it is therefore possible to obtain a more highly accurate ultrasonic image.

6. Third Configuration Example of Ultrasonic Measuring Device

In the case where a thin film piezoelectric element is used as the ultrasonic transducer element, a dip may occur at a specific frequency that depends on the material or thickness of a back plate in the power spectrum of ultrasound radiated from the element. With a third configuration example of the ultrasonic measuring device 100 of this embodiment, the processing unit 130 detects the presence or absence of such a dip, whereby it is possible to determine whether or not the preliminary processing for identifying the amplitude of the transfer function has been appropriately executed.

Figure 10A:
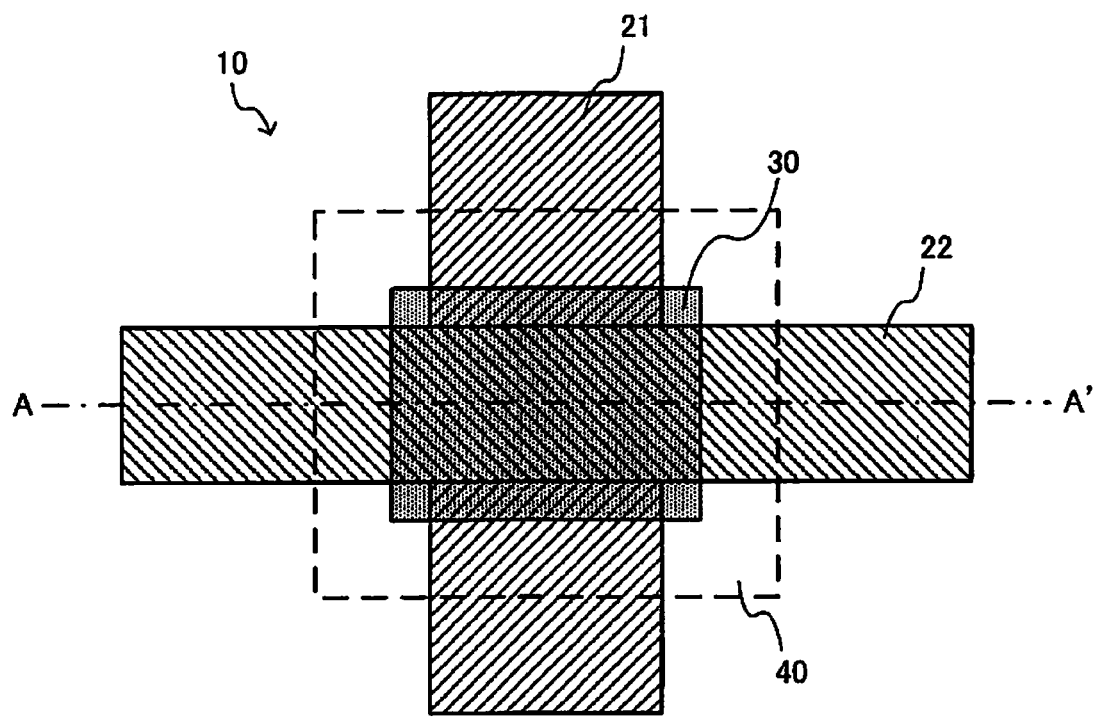
FIGS. 10A and 10B show an example of a basic configuration of an ultrasonic transducer element.
Figure 10B:
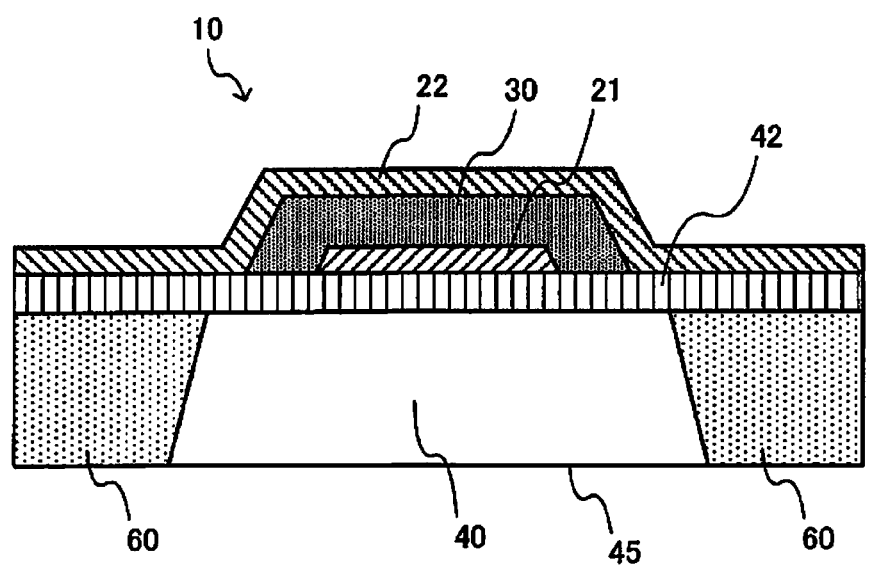

FIGS. 10A and 10B show an example of a basic configuration of an ultrasonic transducer element 10 (thin-film piezoelectric ultrasonic transducer element) of the ultrasonic transducer device 200. The ultrasonic transducer element 10 includes a vibration film 42 and a piezoelectric element unit. The piezoelectric element unit includes a first electrode layer 21, a piezoelectric film 30, and a second electrode layer 22. The configuration of the ultrasonic transducer element 10 of this embodiment is not limited to that shown in FIGS. 10A and 10B, and various modifications can be carried out, such as omitting some of the constituent elements, replacing some of the constituent elements with other constituent elements, and adding other constituent elements.

FIG. 10A is a plan view of the ultrasonic transducer element 10 formed on a substrate 60 (silicon substrate), as viewed from a direction normal to the surface of the substrate on which the element is formed. FIG. 10B is a cross-sectional view showing a cross section taken along the line A-A' shown in FIG. 10A.

The first electrode layer 21 (lower electrode) is formed by a thin metal film on a top layer of the vibration film 42. As shown in FIG. 10A, the first electrode layer 21 may be an interconnect that extends to outside the element forming region and is connected to an adjacent ultrasonic transducer element 10.

The piezoelectric film 30 (piezoelectric layer) is formed by, for example, a PZT (lead zirconate titanate) thin film provided so as to cover at least a part of the first electrode layer 21. The material of the piezoelectric film 30 is not limited to PZT, and it is also possible to use, for example, lead titanate ($PbTiO_3$), lead zirconate ($PbZrO_3$), lead lanthanum titanate (($Pb$, $La$)$TiO_3$), and the like.

The second electrode layer 22 (upper electrode) is formed by, for example, a thin metal film provided so as to cover at least a part of the piezoelectric film 30. As shown in FIG. 10A, the second electrode layer 22 may be an interconnect that extends to outside the element forming region and is connected to an adjacent ultrasonic transducer element 10.

The vibration film 42 (membrane) has a two-layer structure of, for example, a $SiO_2$ thin film and a $ZrO_2$ thin film, and is provided so as to close an opening 45. The vibration film 42 supports the piezoelectric film 30 and the first and second electrode layers 21 and 22, and is capable of generating ultrasound by being vibrated by extension and contraction of the piezoelectric film 30.

The opening 45 is provided in the substrate 60. A hollow region 40 formed by the opening 45 is formed by etching the back surface (the surface on which the element is not formed) of the substrate 60 by reactive ion etching (RIE) or the like. The resonance frequency of ultrasound is determined by the size of the vibration film 42 allowed to vibrate as a result of the hollow region 40 being formed, and the ultrasound is radiated toward the piezoelectric film 30 (from the rear side toward the front in FIG. 10A).

The lower electrode of the ultrasonic transducer element 10 is formed by the first electrode layer 21, and the upper electrode thereof is formed by the second electrode layer 22. Specifically, a portion of the first electrode layer 21 that is covered by the piezoelectric film 30 serves as the lower electrode, and a portion of the second electrode layer 22 that covers the piezoelectric film 30 serves as the upper electrode. That is, the piezoelectric film 30 is sandwiched between the lower electrode and the upper electrode.

The piezoelectric film 30 extends and contracts in an in-plane direction by application of voltage between the lower electrode and the upper electrode, or in other words, between the first electrode layer 21 and the second electrode layer 22. The ultrasonic transducer element 10 has a monomorph (unimorph) structure in which a thin piezoelectric element unit and a vibration film 42 are bonded together, and thus when the piezoelectric element unit extends and contracts within the plane, the vibration film 42 bonded thereto is curved because the size of the vibration film 42 does not change. Accordingly, application of an alternating current voltage to the piezoelectric film 30 causes the vibration film 42 to vibrate in a thickness direction thereof, thereby ultrasound is radiated by the vibrations of the vibration film 42. The voltage applied to the piezoelectric film 30 is, for example, 10 to 30 V, and the frequency is, for example, 1 to 10 MHz.

A bulk ultrasonic transducer element has a peak-to-peak driving voltage of approximately 100 V, but the peak-to-peak driving voltage of the thin-film piezoelectric ultrasonic transducer element as shown in FIGS. 10A and 10B can be reduced to approximately 10 to 30 V.

The ultrasonic transducer element 10 also functions as a reception element that receives an ultrasonic echo obtained as a result of ultrasound being radiated from the element and reflected back from the target subject. The ultrasonic echo causes the vibration film 42 to vibrate, and in response to the vibration, stress is applied to the piezoelectric film 30 to generate voltage between the lower electrode and the upper electrode. The generated voltage can be taken out as a reception signal.

The back surface (the surface on which the element is not formed) of the substrate 60 is provided with a back plate (reinforcing member) (not shown). The back plate is a member for reinforcing the substrate 60 to protect it from mechanical impact. Due to part of ultrasound being absorbed by the back plate, a dip occurs at a specific frequency that depends on the material or thickness of the back plate.

Figure 11:
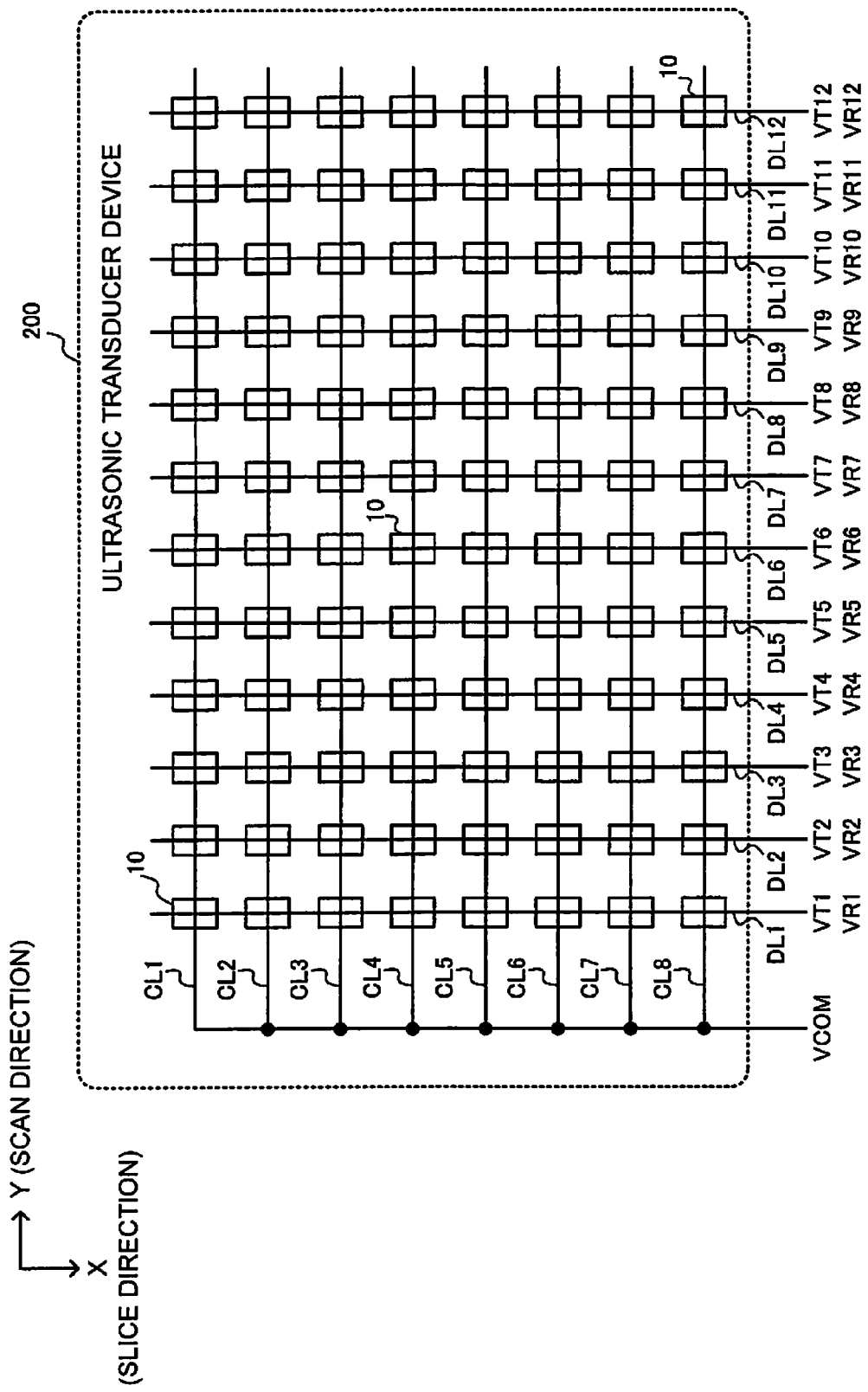
FIG. 11 shows a configuration example of an ultrasonic transducer device.

FIG. 11 shows a configuration example of the ultrasonic transducer device 200 of this embodiment. The ultrasonic transducer device 200 of this configuration example includes a plurality of ultrasonic transducer elements 10 arranged in an array, first to n-th (where n is an integer of 2 or greater) driving electrode lines DL1 to DLn, and first to m-th (where m is an integer of 2 or greater) common electrode lines CL1 to CLm. FIG. 11 shows an example in which m=8, and n=12, but they may take values other than these. Note that the configuration of the ultrasonic transducer device 200 of this embodiment is not limited to that shown in FIG. 11, and various modifications can be carried out, such as omitting some of the constituent elements, replacing some of the constituent elements with other constituent elements, and adding other constituent elements.

The plurality of ultrasonic transducer elements 10 are arranged in a matrix having m rows and n columns. For example, as shown in FIG. 11, eight rows are provided in the X direction, and twelve columns are provided in a Y direction intersecting the X direction. The ultrasonic transducer elements 10 may have a configuration as shown in FIGS. 10A and 10B, for example.

First to twelfth (n-th in a broad sense) driving electrode lines DL1 to DL12 are disposed in the X direction. Among the first to twelfth driving electrode lines DL1 to DL12, a j-th (where j is an integer that satisfies $1 \leq j \leq 12$) driving electrode line DLj is connected to first electrodes of the ultrasonic transducer elements 10 disposed in the j-th column.

During an emission period in which ultrasound is radiated, first to twelfth emission signals VT1 to VT12 output by an emission unit 110, which will be described later, are supplied to respective ultrasonic transducer elements 10 via the driving electrode lines DL1 to DL12. During a reception period in which ultrasonic echo signals are received, reception signals VR1 to VR12 from the ultrasonic transducer elements 10 are output to a reception unit 120, which will be described later, via the driving electrode lines DL1 to DL12.

First to eighth (m in a broad sense) common electrode lines CL1 to CL8 are provided in the Y direction. A second electrode of an ultrasonic transducer element 10 is connected to any one of the first to m-th common electrode lines CL1 to CLm. Specifically, for example, as shown in FIG. 11, among the first to eighth common electrode lines CL1 to CL8, an i-th (where i is an integer that satisfies $1 \leq i \leq 8$) common electrode line CLi is connected to the second electrodes of the ultrasonic transducer elements 10 disposed in the i-th column.

A common voltage VCOM is supplied to the first to eighth common electrode lines CL1 to CL8. It is sufficient that the common voltage is a constant direct current voltage, and it does not necessarily need to be 0 V, or in other words, the ground potential (earth potential).

For example, with respect to the ultrasonic transducer element 10 located in the first column of the first row, its first electrode is connected to the driving electrode line DL1, and its second electrode is connected to the first common electrode line CL1. Likewise, with respect to the ultrasonic transducer element 10 located in, for example, the sixth column of the fourth row, its first electrode is connected to the sixth driving electrode line DL6, and its second electrode is connected to the fourth common electrode line CL4.

The arrangement of the ultrasonic transducer elements 10 is not limited to the arrangement in a matrix having m rows and n columns shown in FIG. 11. It is possible to use a so-called staggered arrangement in which, for example, m ultrasonic transducer elements 10 are arranged in odd number columns, and m−1 ultrasonic transducer elements 10 are arranged in even number columns.

The elements in which a dip occurs in the frequency characteristics of the radiated ultrasound due to the back plate are not limited to the above-described thin film piezoelectric elements, and may be other thin film elements such as, for example, capacitive micromachined ultrasonic transducer (CMUT) elements.

Figure 12:
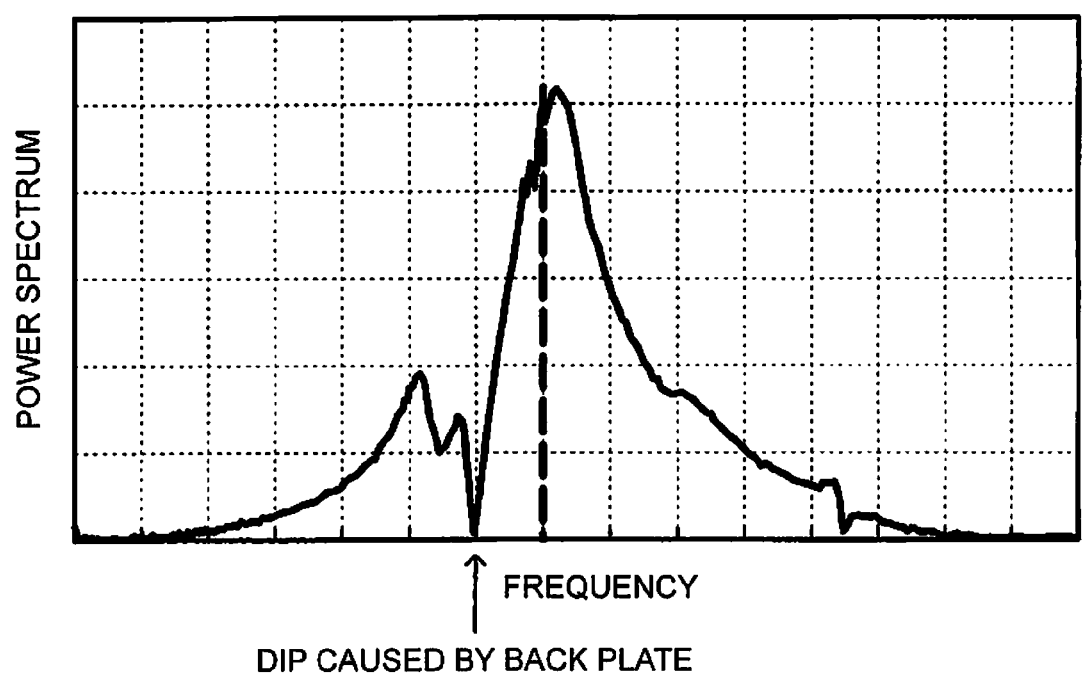
FIG. 12 shows an example of a power spectrum of ultrasound radiated from a thin-film piezoelectric ultrasonic transducer element.

FIG. 12 shows an example of a power spectrum of ultrasound radiated from a thin-film piezoelectric ultrasonic transducer element. As can be seen from FIG. 12, the occurrence of a significant dip is observed at a specific frequency. The frequency at which the dip is observed depends on the material or thickness of the back plate.

As shown in FIGS. 3A and 3B, the power spectra of reception signals include dips caused by interference of a plurality of reflected ultrasonic waves from the test subject, but such dips can be smoothened by averaging the power spectra. In the case of a dip caused due to the back plate as shown in FIG. 12 as well, the dip can be removed by averaging the power spectra. Accordingly, in processing for determining the amplitude of the transfer function (for example, step S7 shown in FIG. 7), if a dip is observed as a result of the power spectra PS1 to PSn being averaged, it indicates a possibility that some kind of problem has occurred in the ultrasonic measurement, or in the analysis of reception signals.

Figure 13:
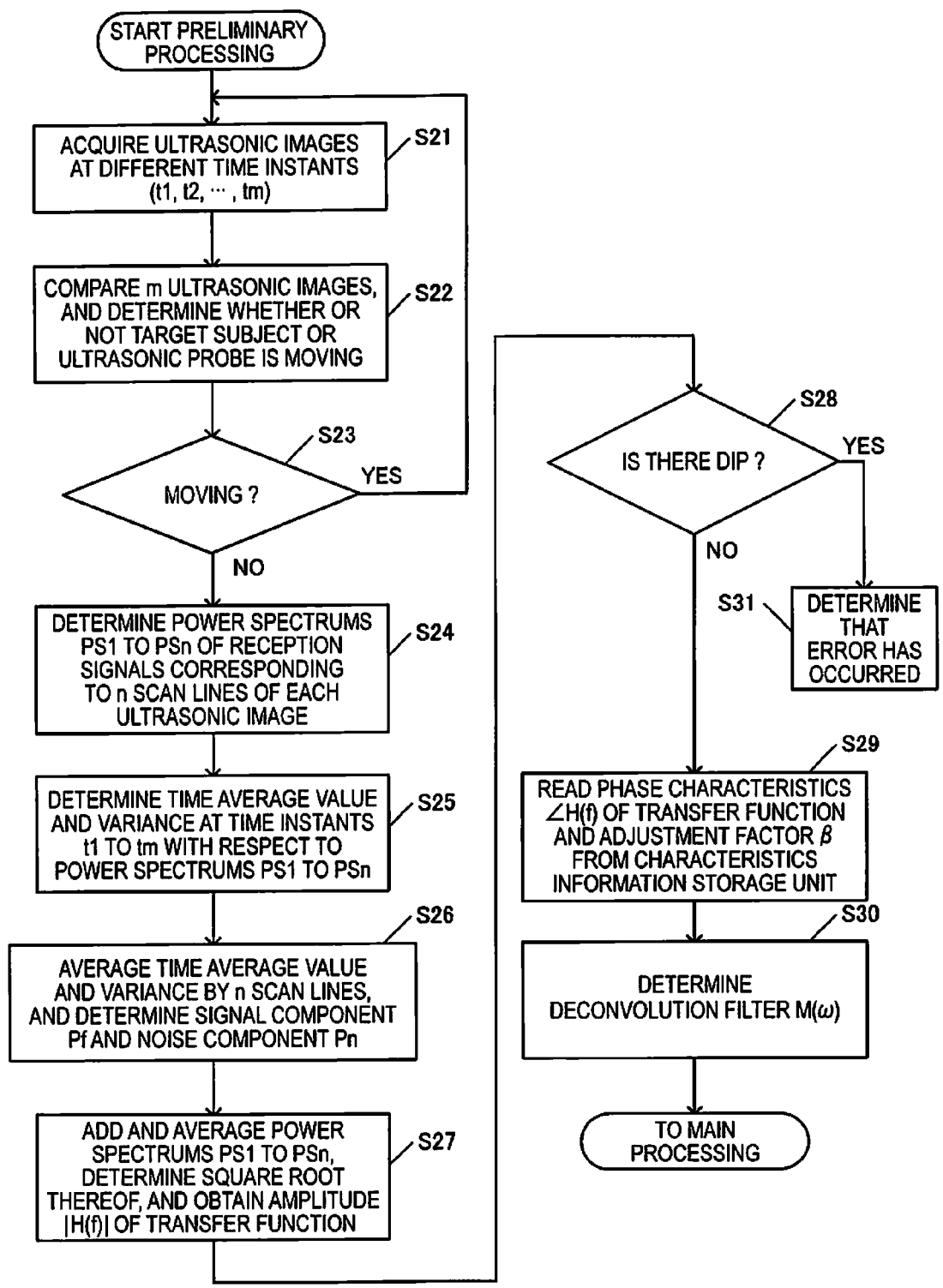
FIG. 13 shows an example of a flowchart of preliminary processing according to a third configuration example.

FIG. 13 shows an example of a flowchart of preliminary processing according to the third configuration example. The processing shown in FIG. 13 is executed by the processing unit 130. Processing in steps S21 to S27 shown in FIG. 13 is the same as the processing (steps S1 to S7 shown in FIG. 7) according to the first configuration example described above, and thus a detailed description thereof is not given here.

The processing unit 130 determines whether or not there is a dip in the result obtained by averaging the power spectra PS1 to PSn (step S28). Specifically, for example, if a $P_{dip}/P_{peak}$ ratio, which is the ratio between a power value $P_{dip}$ at each frequency and a peak power value $P_{peak}$, is smaller than a predetermined value Pa, the processing unit 130 determines that there is a dip. If, on the other hand, the $P_{dip}/P_{peak}$ ratio is greater than or equal to the predetermined value Pa, the processing unit 130 determines that there is no dip.

If the processing unit 130 determines that there is no dip, the processing unit 130 reads, from the characteristics information storage unit 150, the phase characteristics ∠H(f) of the transfer function and the adjustment factor value β (step S29), and determines a deconvolution filter M(ω) (step S30). If, on the other hand, the processing unit 130 determines that there is a dip, the processing unit 130 determines that an error has occurred (step S31), and performs processing such as displaying a screen informing the user of the occurrence of the error on the display unit 410.

As described above, with the third configuration example of the ultrasonic measuring device 100 of this embodiment, the presence or absence of a dip caused due to the back plate is detected by the processing unit 130, and thus it is possible to determine whether or not the preliminary processing has been appropriately executed. Consequently, highly reliable ultrasonic measurement can be performed.

7. Ultrasonic Image Device

Figure 14A:
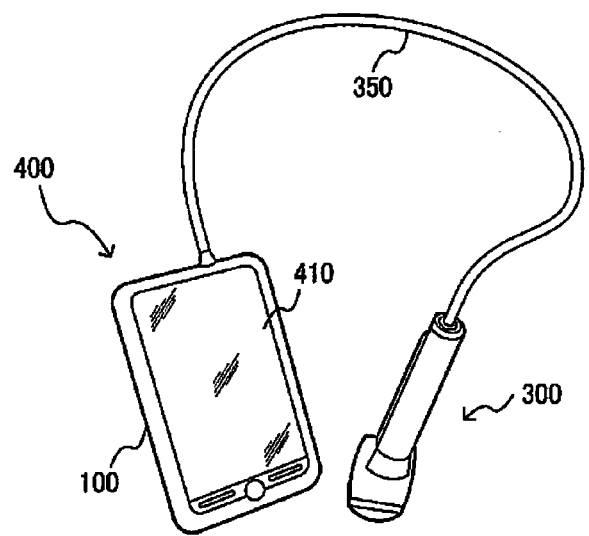
FIGS. 14A and 14B show examples of specific configurations of ultrasonic image devices.
Figures 14B, 14C:
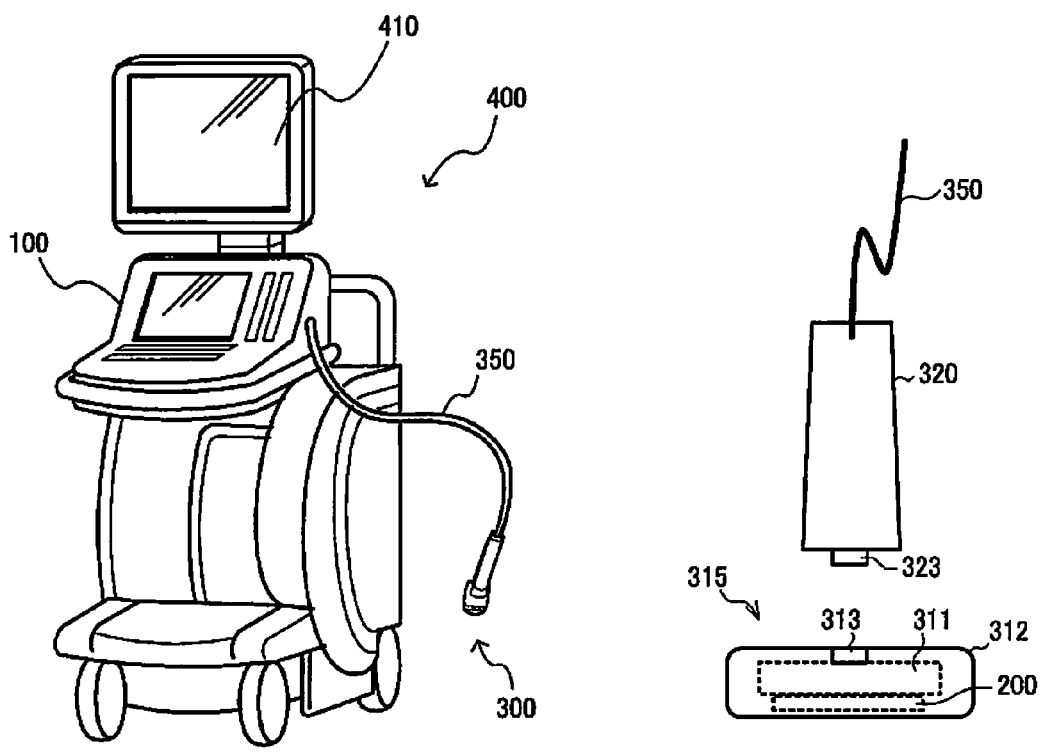
FIG. 14C shows an example of a specific configuration of an ultrasonic probe.

FIGS. 14A and 14B show examples of specific configurations of the ultrasonic image device 400 of this embodiment. FIG. 14A shows a portable ultrasonic image device 400, and FIG. 14B shows a stationary ultrasonic image device 400.

The portable and stationary ultrasonic image devices 400 both include the ultrasonic measuring device 100, an ultrasonic probe 300, a cable 350, and the display unit 410. The ultrasonic probe 300 includes the ultrasonic transducer device 200 and is connected to the ultrasonic measuring device 100 via the cable 350. The display unit 410 displays display image data.

At least a portion of the emission unit 110, the reception unit 120, and the processing unit 130 of the ultrasonic measuring device 100 can be provided in the ultrasonic probe 300.

FIG. 14C shows an example of the specific configuration of the ultrasonic probe 300 of this embodiment. The ultrasonic probe 300 includes a probe head 315 and a probe body 320, and as shown in FIG. 14C, the probe head 315 is detachable from the probe body 320.

The probe head 315 includes the ultrasonic transducer device 200, a probe base 311, a probe housing 312, and a probe head-side connector 313.

The probe body 320 includes a probe body-side connector 323. The probe body-side connector 323 is connected to the probe head-side connector 313. The probe body 320 is connected to the ultrasonic measuring device 100 via the cable 350. Note that at least a portion of the emission unit 110 and the reception unit 120 of the ultrasonic measuring device 100 can be provided in the probe body 320.

Note that although various embodiments have been explained in detail above, a person skilled in the art will readily appreciate that it is possible to implement numerous variations and modifications that do not depart substantially from the novel aspects and effect of the invention. Accordingly, all such variations and modifications are also to be included within the scope of the invention. For example, terms that are used within the description or drawings at least once together with broader terms or alternative synonymous terms can be replaced by those other terms at other locations as well within the description or drawings. Also, the configuration and operation of the ultrasonic measuring device and the ultrasonic image device, and the method for processing an ultrasonic image are not limited to those described in the embodiments, and various modifications are possible.

The entire disclosure of Japanese Patent Application No. 2013-116175, filed May 31, 2013 is expressly incorporated by reference herein.

What is claimed is:

1. An ultrasonic measuring device comprising:
an ultrasonic transducer device; and
a processor configured to
perform processing for emitting an ultrasonic beam,
perform processing for receiving an ultrasonic echo, which is obtained as a result of the ultrasonic beam being reflected by a test subject, and
perform processing based on reception signals obtained by receiving the ultrasonic echo,
wherein the processor identifies a transfer function with respect to the ultrasonic transducer device and the test subject based on a first reception signal corresponding to an ultrasonic echo of an ultrasonic beam radiated to a first area in the test subject, a second reception signal corresponding to an ultrasonic echo of an ultrasonic beam radiated to a second area in the test subject, and a third reception signal corresponding to an ultrasonic echo of an ultrasonic beam radiated to a third area in the test subject, the third area being located between the first area and the second area, and
performs ultrasonic image generation processing including filter processing using a deconvolution filter including the transfer function performed on the reception signals.

2. The ultrasonic measuring device according to claim 1, wherein the processor obtains a first power spectrum of the first reception signal, a second power spectrum of the second reception signal, and a third power spectrum of the third reception signal, and
determines an amplitude of the transfer function from the first power spectrum, the second power spectrum, and the third power spectrum.

3. The ultrasonic measuring device according to claim 2, comprising:
a storage device that stores information regarding phase characteristics of a transfer function with respect to the ultrasonic transducer device,
wherein the processor performs the filter processing using a deconvolution filter by using the information regarding phase characteristics of the transfer function with respect to the ultrasonic transducer device stored in the storage device, and the amplitude of the transfer function determined from the first reception signal, the second reception signal, and the third reception signal.

4. The ultrasonic measuring device according to claim 3, wherein $M(\omega)=H^*(\omega)/(|H(\omega)|^2+\beta\times Pn(\omega)/Pf(\omega))$, where $\omega$ represents an angular frequency, $|H(\omega)|$ represents the amplitude of the transfer function, $H^*(\omega)$ represents a complex conjugate of the transfer function, $Pn(\omega)$ represents a power spectrum of noise components of the reception signals, $Pf(\omega)$ represents a power spectrum of signal components of the reception signals, $\beta$ represents an adjustment factor value, and $M(\omega)$ represents the deconvolution filter.

5. The ultrasonic measuring device according to claim 4, wherein the storage device further stores the adjustment factor value $\beta$, and
the processor performs the filter processing using a deconvolution filter by using the adjustment factor value $\beta$ stored in the storage device.

6. The ultrasonic measuring device according to claim 5, wherein the storage device stores, as the adjustment factor value $\beta$, different values depending on the ultrasonic transducer device or the test subject.

7. The ultrasonic measuring device according to claim 6, wherein the processor performs the filter processing using a deconvolution filter by using the adjustment factor value $\beta$ that varies depending on the ultrasonic transducer device or the test subject.

8. The ultrasonic measuring device according to claim 4, wherein the adjustment factor value $\beta$ is 0.2 or less.

9. The ultrasonic measuring device according to claim 4, comprising:
an input device that receives input of information regarding the adjustment factor value $\beta$,
wherein the processor performs the filter processing using a deconvolution filter by using the information regarding the adjustment factor value $\beta$ received by the input device.

10. The ultrasonic measuring device according to claim 4, wherein the processor determines the power spectrum $Pf(\omega)$ of the signal components based on time average values of power spectra of a plurality of reception signals measured at different time instants, and
determines the power spectrum $Pn(\omega)$ of the noise components based on variances of the power spectra of the plurality of reception signals measured at the different time instants.

11. The ultrasonic measuring device according to claim 1, wherein the processor identifies a first transfer function to an n-th transfer function with respect to a first area to an n-th area (where n is an integer of 2 or greater) that have different depths in the test subject, and performs the filter processing by using a first deconvolution filter to an n-th deconvolution filter including the first transfer function to the n-th transfer function with respect to the first area to the n-th area.

12. The ultrasonic measuring device according to claim 1, wherein the first area in the test subject is an area corresponding to a first edge of the ultrasonic image,
the second area in the test subject is an area corresponding to a second edge of the ultrasonic image that is located opposite to the first edge, and
the third area in the test subject is an area located between the first edge and the second edge in the ultrasonic image.

13. An ultrasonic image device comprising:
the ultrasonic measuring device according to claim 1; and
a display device that displays the ultrasonic image.

14. An ultrasonic image device comprising:
the ultrasonic measuring device according to claim 2; and
a display device that displays the ultrasonic image.

15. An ultrasonic image device comprising:
the ultrasonic measuring device according to claim 3; and
a display device that displays the ultrasonic image.

16. An ultrasonic image device comprising:
the ultrasonic measuring device according to claim 4; and
a display device that displays the ultrasonic image.

17. An ultrasonic image device comprising:
the ultrasonic measuring device according to claim 5; and
a display device that displays the ultrasonic image.

18. An ultrasonic image device comprising:
the ultrasonic measuring device according to claim 6; and
a display device that displays the ultrasonic image.

19. An ultrasonic image device comprising:
the ultrasonic measuring device according to claim 7; and
a display device that displays the ultrasonic image.

20. An ultrasonic image processing method executed by a processor of an ultrasonic measuring device including: an ultrasonic transducer device; and the processor that performs processing for emitting an ultrasonic beam, that performs processing for receiving an ultrasonic echo, which is obtained as a result of the ultrasonic beam being reflected by a test subject and that performs processing based on reception signals obtained by receiving the ultrasonic echo, the method comprising:
identifying a transfer function with respect to the ultrasonic transducer device and the test subject based on a first reception signal corresponding to an ultrasonic echo of an ultrasonic beam radiated to a first area in the test subject, a second reception signal corresponding to an ultrasonic echo of an ultrasonic beam radiated to a second area in the test subject, and a third reception signal corresponding to an ultrasonic echo of an ultrasonic beam radiated to a third area in the test subject, the third area being located between the first area and the second area, and
performing filter processing using a deconvolution filter including the transfer function on the reception signals.

* * * * *